(12) United States Patent
Usagawa

(10) Patent No.: US 9,484,448 B2
(45) Date of Patent: Nov. 1, 2016

(54) SEMICONDUCTOR GAS SENSOR AND METHOD FOR PRODUCING THE SAME

(71) Applicant: Hitachi, Ltd., Chiyoda-ku, Tokyo (JP)

(72) Inventor: Toshiyuki Usagawa, Urawa (JP)

(73) Assignee: Hitachi, Ltd., Tokyo (JP)

(*) Notice: Subject to any disclaimer, the term of this patent is extended or adjusted under 35 U.S.C. 154(b) by 80 days.

(21) Appl. No.: 13/870,189

(22) Filed: Apr. 25, 2013

(65) Prior Publication Data

US 2013/0313569 A1 Nov. 28, 2013

(30) Foreign Application Priority Data

May 22, 2012 (JP) ................................. 2012-116874

(51) Int. Cl.
*H01L 29/78* (2006.01)
*H01L 29/66* (2006.01)
*G01N 27/414* (2006.01)

(52) U.S. Cl.
CPC ........... *H01L 29/78* (2013.01); *G01N 27/4141* (2013.01); *H01L 29/66477* (2013.01)

(58) Field of Classification Search
CPC ......................... H01L 29/517; G01N 27/416
See application file for complete search history.

(56) References Cited

U.S. PATENT DOCUMENTS

| | | | |
|---|---|---|---|
| 5,739,541 A | 4/1998 | Kahilainen | |
| 6,717,271 B2 | 4/2004 | Makiyama et al. | |
| 2001/0045667 A1* | 11/2001 | Yamauchi et al. | 257/774 |
| 2008/0070089 A1 | 3/2008 | Nomura | |
| 2012/0047995 A1 | 3/2012 | Fleischer et al. | |
| 2013/0186178 A1 | 7/2013 | Usagawa | |

FOREIGN PATENT DOCUMENTS

| | | |
|---|---|---|
| CN | 102439432 A | 5/2012 |
| JP | 9-507568 A | 7/1997 |
| JP | 2008-74640 A | 4/2008 |
| JP | 2009-300297 | * 12/2009 |
| JP | 2009-300297 A | 12/2009 |
| JP | 2012-73154 A | 4/2012 |
| WO | WO 2012/043071 A1 | 4/2012 |

OTHER PUBLICATIONS

Toshiyuki Usagawa et al., "Device Characteristics for Pt—Ti—O gate Si-MISFETs Hydrogen Gas Sensors", Sensors and Actuators B:Chemical, 2011, pp. 105-114, vol. 160, Japan.
A. Baranzahi et al., "Gas Sensitive Field Effect Devices for High Temperatures", Sensors and Actuators B, 1995, pp. 165-169, vol. 26-27, Sweden.
Reza Loloee et al., "Hydrogen Monitoring for Power Plant Applications Using SiC Sensors", Sensors and Actuators B, 2008, pp. 200-210, vol. 129, USA.
I. Lundstroem et al., "A Hydrogen-Sensitive MOS Field-Effect Transistor", Applied Physics Letters, Jan. 15, 1975, vol. 26, No. 2, USA (Four (4) pages).
Toshiyuki Usagawa et al., "A Pt—Ti—O Gate Si-Metal-Insulator-Semiconductor Field-Effect Transistor Hydrogen Gas Sensor", Journal of Applied Physics, 2010, vol. 108, Japan (Eight (8) pages).
Chinese Office Action dated Nov. 21, 2014 (ten (10) pages).
Japanese Office Action issued in counterpart Japanese Application No. 2012-116874 dated Aug. 25, 2015, with English translation (eleven (11) pages).
Toshiyuki Usagawa et al., "A Novel Pt—Ti—O gate Si-MISFETs Hydrogen Gas Sensor", Chemical Sensors, Sep. 2, 2010, vol. 26 Supplement B, pp. 91-93, with partial English translation.

* cited by examiner

*Primary Examiner* — Thao X Le
*Assistant Examiner* — Geoffrey Ida
(74) *Attorney, Agent, or Firm* — Crowell & Moring LLP

(57) ABSTRACT

A technique capable of realizing a semiconductor gas sensor having a high rising response speed is provided. A gate insulating film (e.g., a $SiO_2$ film) is formed on a Si layer, and a modified TiOx (a TiOx nanocrystal) film is formed on the gate insulating film. Further, on the modified TiOx film, a Pt film is formed. This Pt film is composed of a plurality of Pt crystal grains, and in a crystal grain boundary gap existing among the plurality of Pt crystal grains, Ti and oxygen (O) are present, and particularly, a TiOx nanocrystal is formed on a surface in the vicinity of a grain boundary triple point as the center.

12 Claims, 15 Drawing Sheets

SEMICONDUCTOR GAS SENSOR AND METHOD FOR PRODUCING THE SAME

This application claims the priority of Japanese Patent Application No. JP 2012-116874, filed May 22, 2012, the disclosure of which is expressly incorporated by reference herein in its entirety.

BACKGROUND OF THE INVENTION

1. Field of the Invention

The present invention relates to a gas sensor using a semiconductor material (a semiconductor gas sensor) and a technique for producing the same, and particularly relates to a semiconductor gas sensor, which is suitable for detecting hydrogen gas, has high reliability and high sensitivity, and can be applied also to an operation in a high temperature environment, and an effective technique to be applied to the production thereof.

2. Background Art

As a gas sensor to be used for detecting hydrogen gas, there are provided a Si-MOSFET (a metal-oxide-semiconductor field-effect transistor) type gas sensor having a Pd (palladium) gate structure (e.g., I. Lundstrom et al., Applied Physics Letters, Vol. 26, No. 2, 15 January, 55-57 (1975) (NPL 1)), and a Si-MOSFET-type gas sensor using Pt (platinum) or another metal in the platinum group as a gate metal. However, such a gas sensor has a problem of lack of reliability (e.g., Introduction of T. Usagawa et al., Journal of Applied Physics, Vol. 108, 074909 (2010) (NPL 2)). Therefore, in the case of a Pt gate structure, in order to prevent the lack of reliability and the contamination of a device in a process line due to film peeling, it is necessary to insert a metal film made of Ti (titanium), Mo (molybdenum), or the like as an adhesive film between a Pt film and a gate insulating film (e.g., a $SiO_2$ (silicon oxide) film). However, the insertion of such an adhesive film caused a problem that the gas sensor does not respond to hydrogen.

Therefore, in order to solve the problem, there has been developed a MISFET (metal-insulator-semiconductor field-effect transistor) type gas sensor having a Pt—Ti—O (platinum-titanium-oxygen) gate structure. This MISFET-type gas sensor having a Pt—Ti—O gate structure has been disclosed in, for example, JP-A-2009-300297 (PTL 1), T. Usagawa et al., Sensors and Actuators, B160, 105-114 (2011) (NPL 3), and the above-described NPL 2.

The Pt—Ti—O gate structure has an oxygen-doped Ti film (hereinafter also referred to as a "modified Ti film") formed by mixing oxygen-doped amorphous Ti and amorphous TiOx (titanium oxide) or a TiOx nanocrystal on a gate insulating film (e.g., a $SiO_2$ film), and also has a Pt film on this oxygen-doped Ti film. The Pt film is composed of a plurality of Pt crystal grains, and in a grain boundary region existing among the plurality of Pt crystal grains, Ti and oxygen (O) are present (hereinafter also referred to as a "modified Pt film").

However, in the above-described MISFET-type gas sensor having a Pt—Ti—O gate structure in the related art, the rising response time is several tens to several hundreds of seconds in some cases, and therefore, measures for such a hydrogen response characteristic are needed.

On the other hand, there is a need for a gas sensor to be used in a harsh outside environment, for example, in a containment of a diesel automobile or a nuclear power plant, to detect exhaust gas (e.g., ammonia) or hydrogen gas. In this case, there is a demand for the use of a gas sensor in a serious disaster in which a nuclear power plant or the like is largely destroyed for some reasons or in a high-temperature (e.g., from 300° C. to 900° C.) gas environment in a turbine, a diesel internal-combustion engine, or the like.

However, when the above-described MISFET-type gas sensor having a Pt—Ti—O gate structure in the related art is operated for several tens of days at a temperature of from about 300° C. to 400° C., a phenomenon in which the rising response time is delayed to several hundreds of seconds was observed.

As a hydrogen gas sensor aiming at the operation thereof at a high temperature (e.g., 800° C.), for example, a SiC-MOSFET-type gas sensor using SiC (silicon carbide) (e.g., R. Loloee et al., Sensors and Actuators, B129, 200-210 (2008) (NPL 4)) has been studied.

However, a sensor signal drifts or an unidentified signal of as much as about 0.6 V is detected even at a low concentration (52.2 ppm), and a basic technique for a gate electrode, a passivation film, a source-drain electrode, a heater, etc. capable of operating stably at a high temperature for a long period of time has not been established yet. In particular, other than the problem of reliability attributed to crystallinity, the fact that a gate electrode having high reliability has not been found yet is the biggest obstacle to putting it into practical use.

For example, the biggest obstacle to obtaining reliability of a Pt gate structure is as follows. When the thickness of a Pt film is 100 nm, a void with a size of several micrometers is formed by annealing at 800° C. for several hours in some cases, and when the thickness of a Pt film is 300 nm, a void with a size of several micrometers or a crack is formed by annealing at 700° C. in some cases (e.g., A. Branzahi et al., Sensors and Actuators, B26/27, 165-169 (1995) (NPL 5)). Due to this, a problem arises in sensor signal drift at a high temperature and reproducibility.

SUMMARY OF THE INVENTION

An object (a first object) of the present invention is to provide a semiconductor gas sensor having an extremely high rising response speed and a method for producing the same.

Another object (a second object) of the present invention is to provide a semiconductor gas sensor which can be operated in a high-temperature environment (e.g., from 250° C. to 900° C.) and a method for producing the same.

Still another object (a third object) of the present invention is to provide a semiconductor gas sensor which can be operated in a high-temperature environment (e.g., from 300° C. to 900° C.) without deteriorating the rising response speed and a method for producing the same.

The above and other objects and novel features of the present invention will be apparent from the description of the present specification and the accompanying drawings.

An embodiment of typical aspects of the invention disclosed in the present application will be briefly described below.

This embodiment is a semiconductor gas sensor including: a semiconductor layer; a gate insulating film formed on the semiconductor layer; a crystalline film formed on the gate insulating film; a gate electrode formed on the crystalline film; a source region formed on the semiconductor layer; and a drain region formed on the semiconductor layer. The crystalline film is composed of a modified TiOx film, and the gate electrode has a Pt film or an Ir film composed of a plurality of crystal grains, and in a grain boundary region existing among the plurality of crystal grains of the Pt film or the Ir film, Ti and oxygen (O) are present. The modified TiOx film has a structure in which a TiOx nanocrystal in an oxygen-doped Ti film formed by mixing oxygen-doped amorphous Ti and amorphous TiOx or a TiOx nanocrystal grows large to form a TiOx microcrystalline region, and an oxygen-doped amorphous Ti region is less.

This embodiment includes: a step of forming a gate insulating film on a semiconductor layer; a step of forming a Ti film on the gate insulating film; a step of forming a Pt film or an Ir film composed of a plurality of Pt crystal grains or a plurality of Ir crystal grains on the Ti film, and a step of performing thereafter annealing in an atmosphere containing oxygen (O) at a heat treatment temperature of from 300° C. to 630° C. for a heat treatment time of from 2 hours to 2 years. The Ti film has a thickness of 1 nm or more and 15 nm or less, and the Pt film or the Ir film has a thickness of 1 nm or more and 90 nm or less.

The effects obtained by an embodiment of typical aspects of the invention disclosed in the present application will be briefly described below.

A semiconductor gas sensor which has an extremely high rising response speed and a method for producing the same can be provided.

Further, a semiconductor gas sensor which can be operated in a high-temperature environment (e.g., from 250° C. to 900° C.) and a method for producing the same can be provided.

Further, a semiconductor gas sensor which can be operated in a high-temperature environment (e.g., from 300° C. to 900° C.) without deteriorating the rising response speed and a method for producing the same can be provided.

BRIEF DESCRIPTION OF THE DRAWINGS

FIG. 17A is a TEM photograph of a cross-section of a Pt (15 nm)-Ti (5 nm)/SiO$_2$/Si substrate structure after performing annealing in an air atmosphere at 400° C. for 2 hours, and then performing annealing in an air atmosphere at 600° C. for 12 days. FIG. 17B is a TEM photograph of a cross-section of a Pt (15 nm)-Ti (5 nm)/SiO$_2$/Si substrate structure after performing annealing in an air atmosphere at 400° C. for 2 hours, and then performing annealing in an air atmosphere at 700° C. for 12 days.

DESCRIPTION OF THE PREFERRED EMBODIMENTS

Figure 1:
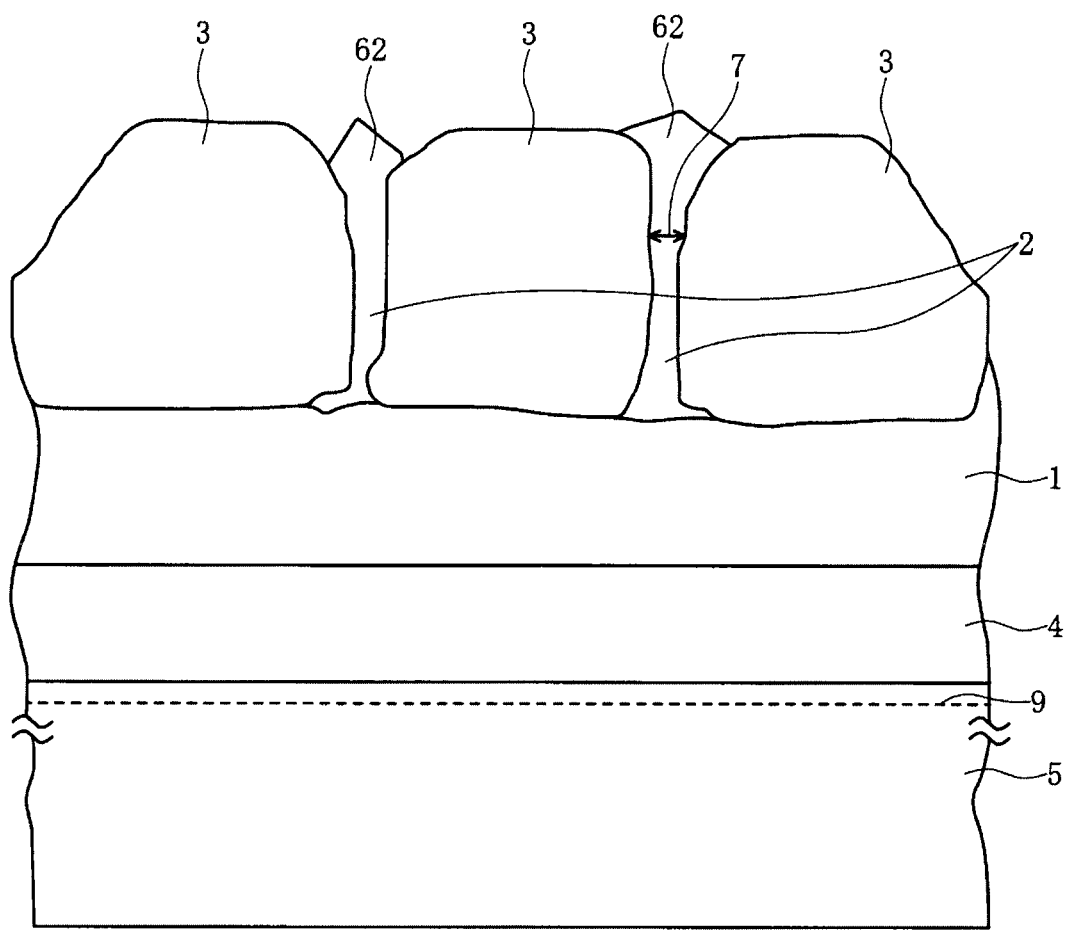
FIG. 1 is an enlarged schematic cross-sectional view of a part of a gate structure of a Si-MISFET having a modified Pt—Ti—O gate structure according to a first embodiment of the invention.

In the embodiments described below, the present invention will be described by being divided into a plurality of sections or embodiments when required as a matter of convenience. However, these sections or embodiments are not irrelevant to each other unless otherwise explicitly stated, and the one relates to the entire or a part of the other as a modification example, details, a supplementary explanation thereof, or the like.

Also, in the embodiments described below, when referring to the number of elements (including number of pieces, numerical value, amount, range, etc.), the number of the elements is not limited to a specific number unless otherwise explicitly stated or except the case where the number is apparently limited to a specific number in principle, and the number larger or smaller than the specific number is also applicable. Further, in the embodiments described below, it goes without saying that the components (including element steps, etc.) are not always indispensable unless otherwise explicitly stated or except the case where it is conceivable that the components are apparently indispensable in principle. Similarly, in the embodiments described below, when the shape of the components, positional relationship thereof, and the like are mentioned, the substantially approximate and similar shapes and the like are included therein unless otherwise explicitly stated or except the case where it is conceivable that they are apparently excluded in principle. The same goes for the numerical value and the range described above.

Also, the "nanocrystal" as used in the embodiments described below refers to a minute crystal having a size of a nanometer (nm) order (generally represents a range of from one nanometer to ten and several nanometers). The nanocrystal is a polycrystal composed of several hundreds to several tens of thousands of crystal atoms, and the size of the nanocrystal is larger than that of a molecule and smaller than that of a bulk crystal.

Also, in the embodiments described below, an oxygen-doped Ti film formed by mixing oxygen-doped amorphous Ti and amorphous TiOx or a TiOx nanocrystal is called a modified Ti film. Further, a film composed mostly of a TiOx microcrystal obtained by allowing a TiOx nanocrystal in a modified Ti film to grow large is called a modified TiOx film, and in this modified TiOx film, by forming a TiOx microcrystalline region, an oxygen-doped amorphous Ti region is reduced.

Also, in some drawings used in the embodiments described below, hatching is sometimes used even in a plan view so as to make the drawings easy to see.

Further, components having the same function are denoted by the same reference numerals in principle in all drawings for explaining the embodiments described below, and the repetitive explanation thereof is omitted. Hereinafter, the embodiments of the present invention will be described in detail based on the drawings.

First, in order to further clarify the structure of the gas sensor according to the embodiments of the invention, the structure and characteristic of a Si-MISFET-type gas sensor having a Pt—Ti—O gate structure in the related art before the invention of the present application is applied, which was examined by the present inventors, and the characteristic of a SiC-MISFET-type gas sensor in the related art will be described as comparative examples.

(1) The structure and characteristic of a Si-MISFET-type gas sensor having a Pt—Ti—O gate structure in the related art, which was examined by the present inventors, will be described with reference to FIGS. 12 to 17B.

For example, as disclosed in the above-described PTL 1 and NPL 2 and NPL 3, the Pt—Ti—O gate structure in the related art is formed by, for example, exposing a Pt/Ti laminate structure (a structure in which a Pt film is laminated on a Ti film) to an oxidation temperature of 400° C., and as the penetration of oxygen (O) into the Ti film, Ti in the Ti film is allowed to flow out to the surface of the Pt film through a Pt crystal grain boundary to reduce stress applied to the Pt film. By doing this, the thickness of the Ti film is maintained substantially constant and peeling of Pt crystal grains is prevented.

Figure 12:
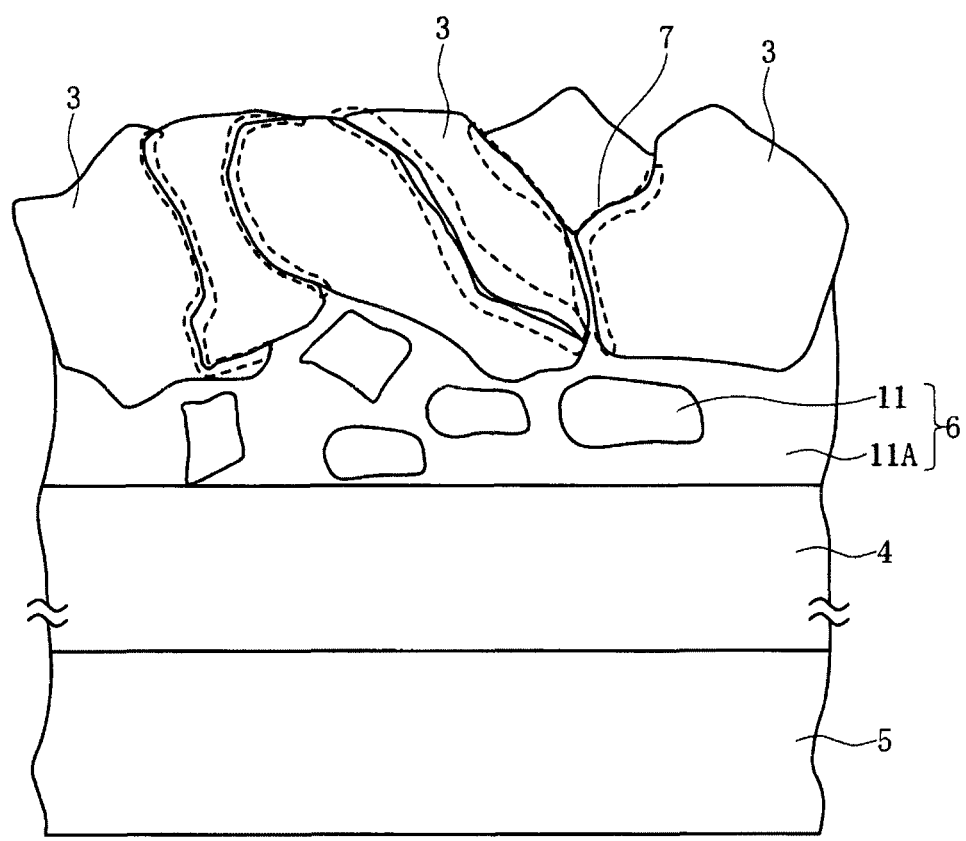
FIG. 12 is an enlarged schematic cross-sectional view of a part of a gate structure of a Si-MISFET having a Pt—Ti—O gate structure examined by the present inventors.

FIG. 12 is an enlarged schematic cross-sectional view of a part of a gate structure of the Si-MISFET having a Pt—Ti—O gate structure in the related art.

On a Si (silicon) layer 5, a gate insulating film 4 (e.g., a $SiO_2$ film) is formed, and on the gate insulating film 4, a modified Ti film 6 is formed. The modified Ti film 6 is an oxygen-doped Ti film formed by mixing oxygen-doped amorphous Ti 11A and amorphous TiOx or a TiOx nanocrystal 11. On this modified Ti film 6, a Pt film (a gate electrode) is formed. This Pt film is composed of a plurality of Pt crystal grains 3, and in a crystal grain boundary gap 7 existing among the plurality of Pt crystal grains 3, Ti and oxygen (O) are present. The modified Ti film 6 also has an effect of maintaining the adhesiveness between the gate insulating film 4 and the Pt film.

Figure 13:
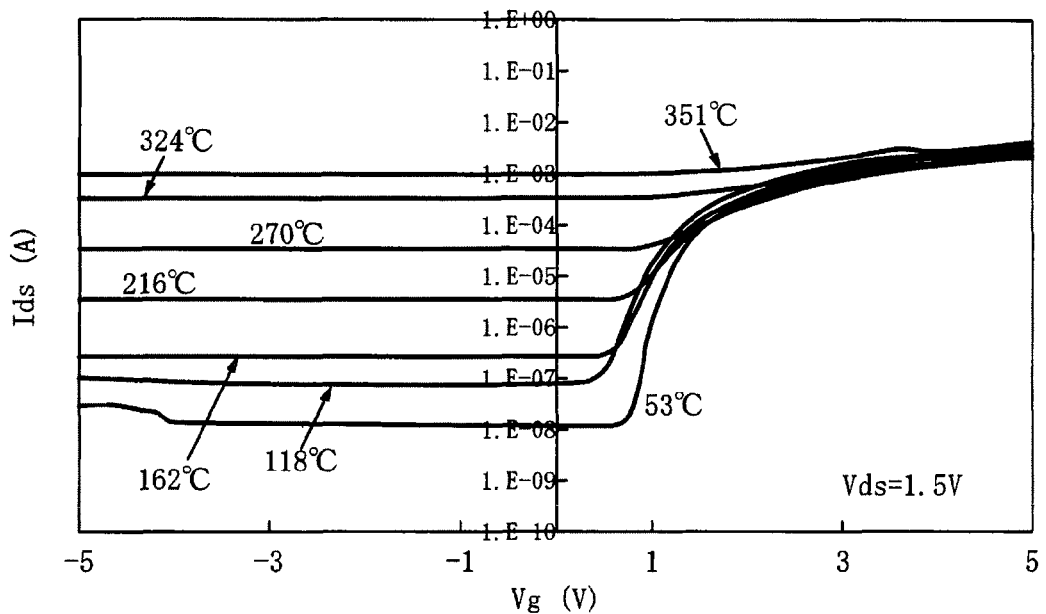
FIG. 13 is a graph for explaining a relationship between a source-drain current (Ids) and a gate voltage (Vg) in the Si-MISFET having a Pt—Ti—O gate structure examined by the present inventors.

FIG. 13 is a graph for explaining a relationship between a source-drain current (Ids) and a gate voltage (Vg) in the Si-MISFET having a Pt—Ti—O gate structure in the related art. The gate length (Lg) is 10 μm and the gate width (Wg) is 150 μm. A source and a p-type well were grounded, a source-drain voltage (Vds) was fixed at 1.5 V, and a source-drain current (Ids) was measured when a gate voltage (Vg) was changed from −5 V to +5 V. The parameter was the operation temperature of the Si-MISFET, and 7 temperature points (53° C., 118° C., 162° C., 216° C., 270° C., 324° C., and 351° C.) were selected in a range of from 53° C. to 351° C. The vertical axis of the graph indicates a source-drain current (Ids), and the horizontal axis thereof indicates a gate voltage (Vg). Here, the measurement result using an n-channel type MISFET is shown, however, a similar measurement result was also obtained using a p-channel type MISFET.

Figure 14:
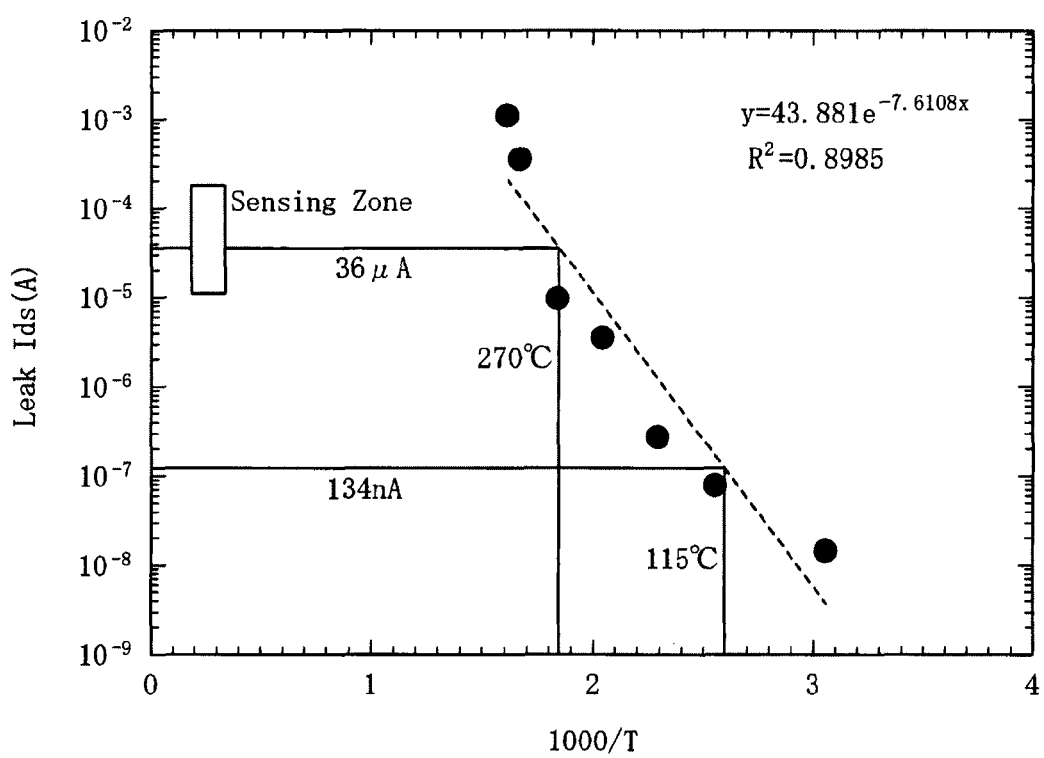
FIG. 14 is a graph for explaining a relationship between a source-drain current (Ids) and an operation temperature (an absolute temperature (T)) in the Si-MISFET having a Pt—Ti—O gate structure examined by the present inventors.

FIG. 14 is a graph for explaining a relationship between a source-drain current (Ids) and an operation temperature (an absolute temperature (T)) when the gate voltage (Vg) was set to −1.5 V and the drain voltage (Vds) was set to 1.5 V in the above-described FIG. 13. The vertical axis of the graph indicates a source-drain current (Ids), and the horizontal axis thereof indicates a ratio of 1000/absolute temperature (T). The dotted line in FIG. 14 represents a least squares fitting function of the data at the seven temperature points measured in the range of from 53° C. to 351° C., and an activation energy obtained from the Arrhenius plot of the dotted line is almost half the band gap of a Si semiconductor.

Generally, in the gas sensing, the source-drain current is used from about 10 μA to 100 μA, and in consideration of also the temperature dependence of the sensor intensity, the upper limit enabling the use thereof as a gas sensor is about 270° C.

Figure 15:
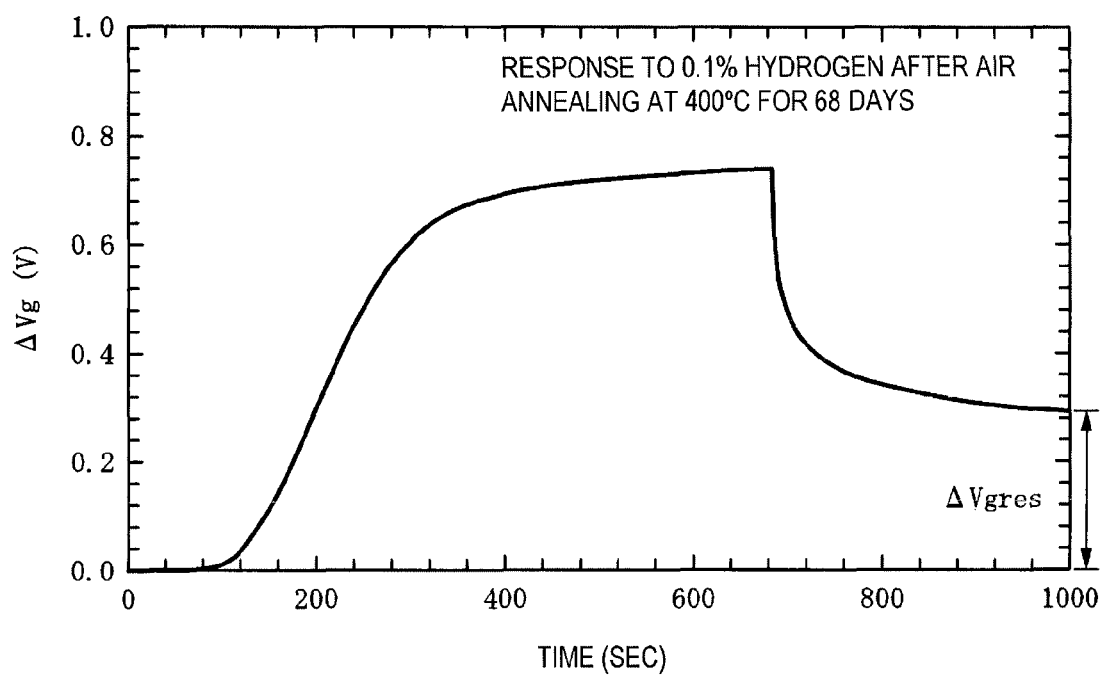
FIG. 15 is a graph for explaining a hydrogen response characteristic when the Si-MISFET having a Pt—Ti—O gate structure examined by the present inventors was annealed in an air atmosphere at 400° C. for 68 days, and thereafter the Si-MISFET was irradiated with 0.1% hydrogen diluted with air.

FIG. 15 is a graph for explaining a hydrogen response characteristic when the Si-MISFET having a Pt—Ti—O gate structure in the related art was annealed in an air atmosphere at 400° C. for 68 days, and thereafter the Si-MISFET was irradiated with 0.1% hydrogen diluted with air (gas irradiation). The vertical axis of the graph indicates a hydrogen response intensity (ΔVg). The thickness of the Pt film is 15 nm, the thickness of the Ti film is 5 nm, and the thickness of the $SiO_2$ film is 18 nm. The operation temperature of the sensor is 115° C.

In the Si-MISFET-type gas sensor, a phenomenon in which terminating hydrogen starts to be desorbed at a temperature from about 300° C. to 400° C. (a phenomenon in which the rising response time at the time of gas irradiation is delayed to about several hundreds of seconds, the threshold voltage (Vth) is significantly shifted, and a residual response intensity (ΔVgres) is generated) occurred. In fact, before performing annealing in an air atmosphere at 400° C. for 68 days, the rising time at the time of gas irradiation was as short as several seconds, and also a residual response time when stopping the gas irradiation was short.

However, by performing annealing in an air atmosphere at 400° C. for 68 days, terminating hydrogen in the vicinity of the boundary surface between the gate insulating film (the $SiO_2$ film) and the semiconductor (Si) is desorbed, and therefore the rising time at the time of gas irradiation is delayed to about 300 seconds and the residual response time when stopping the gas irradiation is prolonged. Further, after the gas irradiation, a phenomenon in which the threshold voltage (Vth) is significantly shifted and fixed, and a residual response intensity (ΔVgres) of about 0.3 V is left occurs.

As for the sample for which the hydrogen response characteristic was measured and the measurement result is shown in FIG. 15, the cross-section thereof was observed by a TEM (a transmission electron microscope).

Figure 16A:
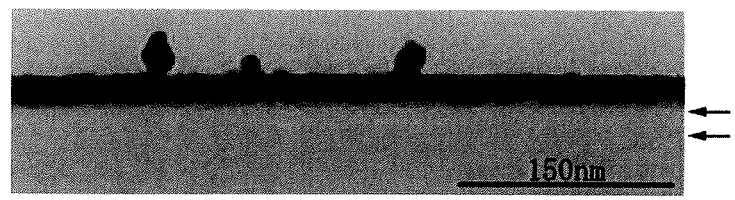
FIGS. 16A to 16C are each a TEM photograph of a cross-section of a modified Pt—Ti—O gate structure after annealing the Si-MISFET having a Pt—Ti—O gate structure examined by the present inventors in an air atmosphere at 400° C. for 68 days.
Figure 16B:
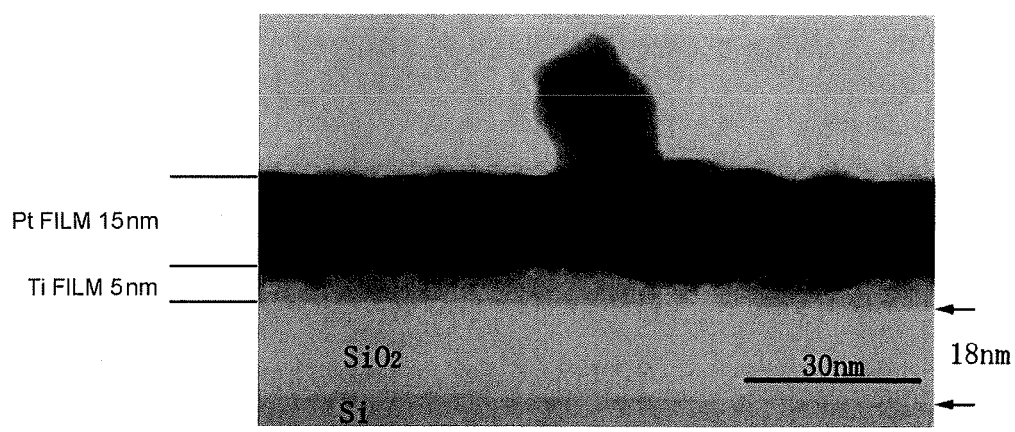
Figure 16C:
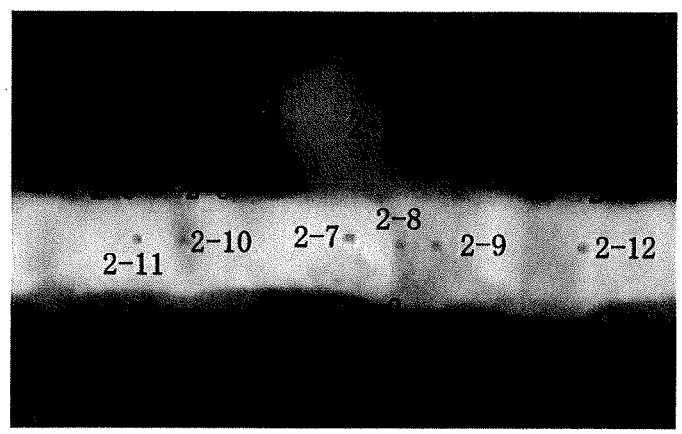

FIGS. 16A to 16C are each a TEM photograph of a cross-section of a modified Pt—Ti—O gate structure after annealing an actually produced MISFET having a Pt—Ti—O gate structure in the related art in an air atmosphere at 400° C. for 68 days. The thickness of the Pt film is 15 nm, the thickness of the Ti film is 5 nm, and the thickness of the SiO$_2$ film is 18 nm.

FIG. 16A and FIG. 16B, which is an enlarged view of FIG. 16A, are each a dark-field image, and it is found that the structure of the Ti film is changed such that a TiOx nanocrystal grows large (to a TiOx microcrystal), and an oxygen-doped amorphous Ti region is significantly reduced (a modified TiOx film).

In this example, from the TEM observation, it can be determined that the ratio of the TiOx microcrystalline region becomes larger than the ratio of the oxygen-doped amorphous Ti region, and the TiOx microcrystalline region accounts for about 75% of the modified TiOx film.

On the other hand, FIG. 16C shows a bright-field image obtained by reversing the bright and dark portions of FIG. 16B. The reference numerals 2-10, 2-8, etc. in FIG. 16C each indicate a portion which looks dark because Ti and oxygen (O) are accumulated at the Pt crystal grain boundary, and also by the TEM-EDX analysis, it is clearly shown that Ti and oxygen (O) are accumulated there. Further, it is found that on the Pt film, a Pt microcrystal 2-1 is partially deposited in a columnar shape from the surface of the Pt film, however, it acts as a singular point on the surface. Such a singular point has a gas catalytic function of decomposing a hydrogen molecule, etc. into hydrogen atoms more efficiently, and therefore has an effect of improving the gas catalytic function as a gas sensor.

(2) The characteristic of a SiC-MISFET-type gas sensor in the related art, which was examined by the present inventors, will be described.

In a SiC semiconductor constituting a SiC-MISFET-type gas sensor, many crystalline polymorphisms exist. By taking 4H—SiC and 3C—SiC, which have been most commonly used, as examples, the band gaps (Eg) of 4H—SiC and 3C—SiC are 3.26 eV and 2.36 eV, respectively, and are about two or three times larger than that of Si, and therefore, even at a high temperature ranging from 300° C. to 1000° C., a leakage current between a source and a drain can be made very small. Therefore, there is a possibility that a gas such as hydrogen gas can be measured in a high-temperature operation environment (from 300° C. to 1000° C.), which will be a big advantage.

A problem of such a SiC-MISFET-type gas sensor is, other than the problem of reliability attributed to crystallinity, to develop a technique capable of operating the gas sensor stably at such a high temperature for a long period of time, particularly a technique for realizing high reliability for a gate electrode.

That is, the SiC-MISFET-type gas sensor having a Pt gate structure in the related art is configured such that a metal (Pt) constituting the gate electrode has a porous structure, and therefore enables gas sensing and can ensure the operation period of from about 5 days to 480 hours. However, sensing gate voltage drift becomes extremely prominent. For example, in FIG. 4 of the above-described NPL 4, even when the concentration of hydrogen is 52.2 ppm, an unidentified sensor signal in the vicinity of 0.6 V is detected, and a drift of about 100 mV was observed in a measurement time of about 1 hour. From the above-described FIG. 4, the drift does not seem to disappear.

It is also found from, for example, the observation result (FIGS. 1 and 4 of the above-described NPL 5) using an SEM (a scanning electron microscope) described in the above-described NPL 5 that Pt (100 nm) has a porous structure. That is, it is considered that the porous structure is a common characteristic of a Pt film having a thickness of about 100 nm heated to a high temperature. According to the above-described NPL 5, in particular, it has been reported that the biggest obstacle to the reliability of a Pt gate structure is as follows: when the thickness of the Pt film is 100 nm, a void with a size of several micrometers is formed by annealing at 800° C. for several hours, and when the thickness of the Pt film is 300 nm, a void with a size of several micrometers or a crack is formed by annealing at 700° C. Even if the Pt film is thick and has a thickness of 300 nm, when the Pt film is a simple Pt film, a void or a crack is formed at a high temperature of 700° C. or higher, which is a cause of a lack of reliability as a gate electrode of a gas sensor.

On the other hand, the present inventors systematically examined at what temperature a Pt grain is peeled off and whether or not avoid is formed when a Pt—Ti—O gate structure was exposed to a high temperature in an atmospheric gas.

As the Pt—Ti—O gate structure of initial value, a thermally oxidized film (a SiO$_2$ film) having a thickness of 124 nm was formed on a Si substrate, and further a Ti film having a thickness of 5 nm and a Pt film having a thickness of 15 nm were formed by an EB method (an electron beam vapor deposition method). Thereafter, annealing was performed in air at 400° C. for 2 hours. Then, annealing in air at 475° C. for 56 days and annealing in air at 600° C., 630° C., 650° C., or 700° C. for 12 days were performed, and cross-sectional TEM photographic observation, surface observation by a SEM, and surface observation by a light microscope were performed.

Figure 17A:
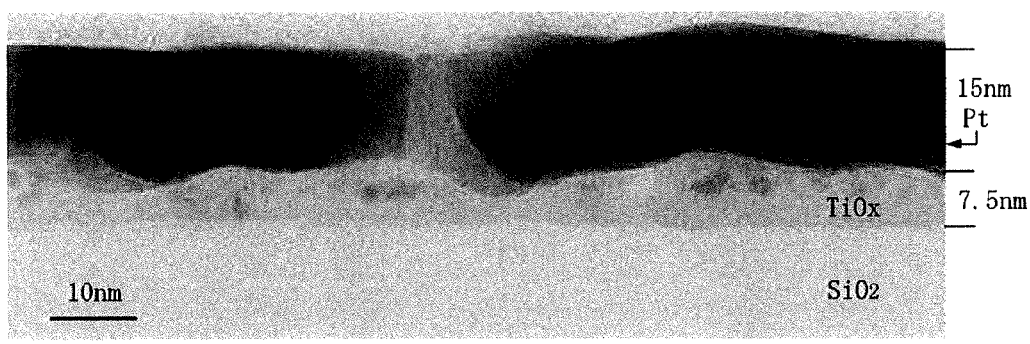
FIGS. 17A and 17B are TEM photographs of cross-sections of respective Pt—Ti gate structures in respective annealing experimental examples.
Figure 17B:
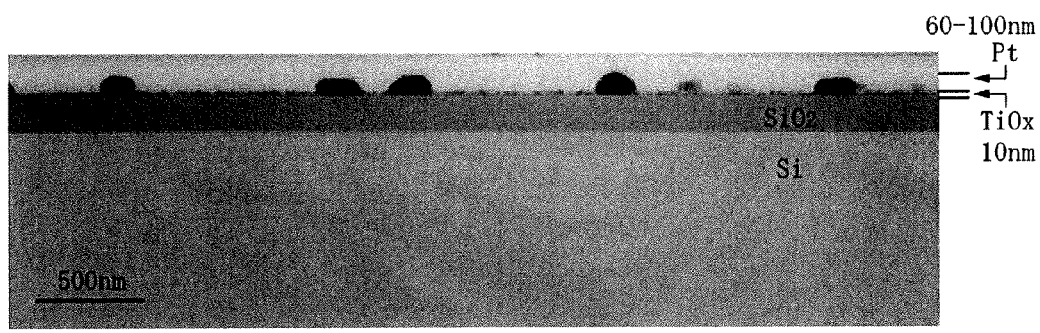

As a result, partial peeling started to be observed at 650° C., and at 700° C., a specific peeling structure in which disk-shaped Pt grains (width: from about 160 nm to 280 nm, height: from about 60 nm to 100 nm) are scattered on the Ti oxide substantially similar to FIG. 19 of the above-described PTL 1 appeared. On the other hand, it was found that at 475° C., 600° C., and 630° C., a modified Pt—Ti—O gate structure can be realized. FIG. 17A shows a TEM photograph of a cross-section of a sample subjected to an annealing treatment at 600° C. for 12 days, and FIG. 17B shows a TEM photograph of a cross-section of a sample subjected to an annealing treatment at 700° C. for 12 days.

In the sample subjected to an annealing treatment at 600° C. for 12 days, as for the ratios of the TiOx microcrystalline region and the oxygen-doped amorphous Ti region, it can be determined from the TEM observation that the ratio of the TiOx microcrystalline region is about 90%. The reason why the ratio of the TiOx microcrystalline region increased as compared with the sample shown in the above-described FIGS. 16A to 16C is considered that the annealing was performed at a higher temperature.

It is considered that annealing of such a Pt thin film having a thickness of about 15 nm at a high temperature in an oxygen atmosphere causes a phenomenon different from the occurrence of a void with a size of several micrometers or a crack in a simple Pt film as shown in the above-described NPL 5. A modified Pt film on a modified Ti film strongly adhering to a gate insulating film (a $SiO_2$ film) is thermally expanded with an increase in the temperature, and the modified Pt film can no longer adhere to the entire surface of the boundary surface with the modified Ti film at a certain temperature, and therefore, it is considered that in the case of a thin film having a thickness of about 15 nm, small peeling occurs partially in the boundary surface between the modified Pt film and the modified Ti film. From the ruptured portion of the modified Pt film in which the peeling occurred, a large amount of oxygen flows into the modified Ti film, and the modified Ti film is converted to a modified TiOx film.

On the other hand, in the case of a Pt thin film having a thickness of about 15 nm, the Pt thin film starts to become a soft film in a state close to a solution at a temperature of about 650° C. (absolute temperature: 923 K), which is quite different from the melting point in a bulk state (Pt: 1774° C., Ti: 1727° C.), and by the surface tension of itself, aggregation is caused to form the above-described disk-shaped Pt grain. Therefore, although Pt itself has a melting point of 1774° C. (absolute temperature: 2047 K), the Pt thin film starts to exhibit a characteristic close to a solution at a temperature of about 650° C. (absolute temperature: 923 K).

Figure 5:
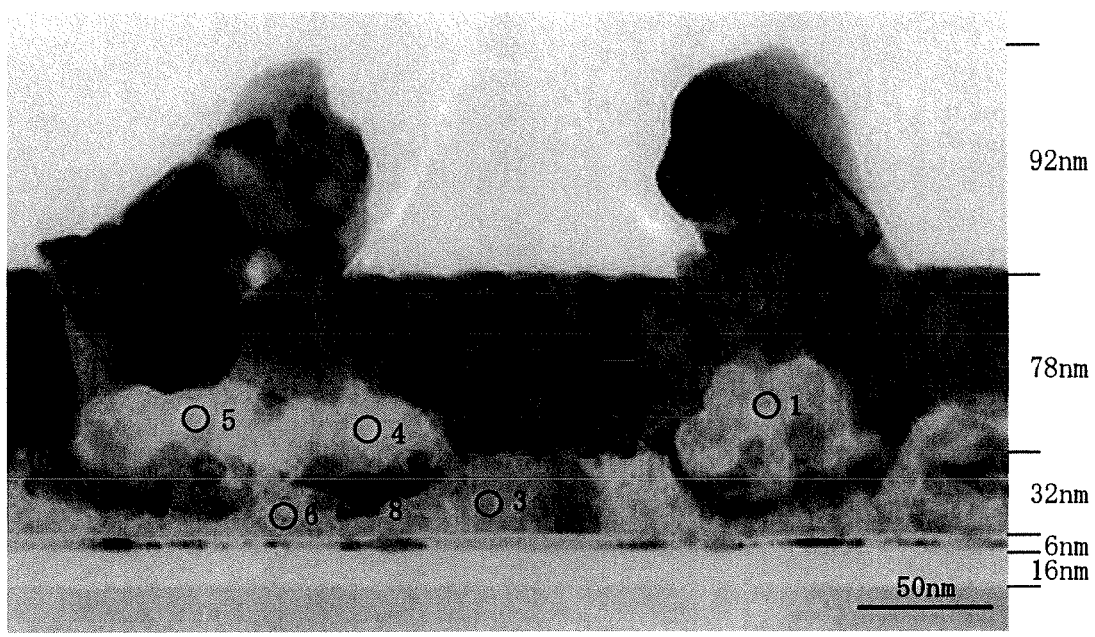
FIG. 5 is a TEM photograph of a cross-section of a Pt—Ti/SiO$_2$/Si substrate after annealing a MISFET having a Pt (78 nm)-Ti (32 nm)/SiO$_2$/Si substrate structure in an air atmosphere at 400° C. for 128 hours.

As shown in FIG. 5 described below, TEM observation and TEM-EDX (energy-dispersive X-ray spectroscopy) analysis were performed for a sample (the thickness of a Pt film is 78 nm and the thickness of a Ti film is 32 nm), which is in a position between a Pt film having a thickness of 15 nm and a Pt film having a thickness of from 100 nm to 300 nm (the above-described NPL 5), and which was annealed in an air atmosphere at 400° C. for 128 hours, and the result is shown in FIG. 5. Incidentally, the gate insulating film of the sample is a $SiO_2$ film and has a thickness of 16 nm.

In this case, peeling of Pt grain aggregates due to stress caused by expansion of the Ti film which absorbed oxygen flowing into a Pt grain boundary is observed. In the case of the above-described NPL 5, a Ti film as an underlayer of the Pt film is not formed, and therefore, it is considered that the mechanism of forming a void with a size of several micrometers or a crack is different even if the annealing is performed at the same temperature of 700° C. That is, a characteristic close to a solution such as aggregation into a disk-shaped Pt grain shown in the example of the TEM photograph of the cross-section of the sample subjected to an annealing treatment at 700° C. for 12 days shown in FIG. 17B is not exhibited.

On the other hand, in the case where a Pt thin film is used, the upper limit temperature at which the modified Pt—Ti—O gate structure can be maintained over a long period of time is 630° C. as discussed above although depending also on the component of the atmospheric gas and the pressure thereof. However, in fact, there is a demand for gas sensing at a temperature up to around 1000° C., at which a SiC semiconductor can be operated, and therefore, realization of a catalytic gate structure which can be stably operated for a long period of time even at 630° C. or higher has been demanded.

In consideration of the reliability of gas sensing, it is not preferred that the gate structure has a void with a size of several micrometers or a crack. Therefore, the present inventors searched for a catalytic gate structure which enables gas sensing at a temperature up to around 1000° C. among structures which do not have a porous structure as described above and are of the same type of the modified Pt—Ti—O gate structure. It is considered that if the above-described way of thinking is right, such a catalytic gate structure can be realized if there is a catalytic metal which is hardly oxidized similarly to Pt and has a melting point higher than Pt.

Therefore, metals (Ru (ruthenium), Rh (rhodium), Pd (palladium), Os (osmium), and Ir (iridium)) which are in the platinum group as with Pt were examined. Ru, Rh, and Pd easily form an oxide, and therefore are excluded from candidates, and Os forms a toxic oxide, although it has a melting point as high as 2700° C., and therefore is also excluded from candidates. Ir has a melting point of 2454° C., which is higher than that of Pt by as much as 680° C. and is not easily oxidized, and therefore is determined to be a promising candidate substance.

Therefore, as an Ir—Ti—O gate structure of initial value, a thermally oxidized film (a $SiO_2$ film) having a thickness of 124 nm was formed on a Si substrate, and further a Ti film having a thickness of 5 nm and an Ir film having a thickness of 15 nm were formed by an EB method (an electron beam vapor deposition method). Thereafter, annealing was performed in air at 400° C. for 2 hours. Then, an annealing treatment in air at 600° C., 700° C., 800° C., 900° C., or 930° C. for 12 days was performed. It was found that a modified Ir—Ti—O gate structure (a structure in which Pt in the modified Pt—Ti—O gate structure was replaced with Ir) is maintained.

Next, a specific Si-MISFET-type gas sensor, a specific SiC-MISFET-type gas sensor, and specific methods for producing the same according to the present embodiment will be described. In a first embodiment, the structure and characteristic of a Si-MISFET-type gas sensor will be described, and in second and third embodiments, the structure and characteristic of a SiC-MISFET-type gas sensor will be described. In a forth embodiment, the characteristics of the respective Si-MISFET-type gas sensor and the SiC-MISFET-type gas sensor will be described.

First Embodiment

The present inventors performed annealing (a heat treatment) of a Si-MISFET having a Pt—Ti—O gate structure in an air atmosphere at 400° C. for 68 days. The thickness of a Pt film is 15 nm, the thickness of a Ti film is 5 nm, and the thickness of a $SiO_2$ film is 18 nm. The gate length (Lg) is 10 µm, and the gate width (Wg) is 150 µm. It was found that by performing this treatment, the structure is changed such that a TiOx nanocrystal (a TiOx microcrystal) in a modified Ti film grows large, and an oxygen-doped amorphous Ti region is significantly reduced (hereinafter, a crystalline film composed of a TiOx nanocrystal (a TiOx microcrystal) is referred to as a modified TiOx film). This phenomenon occurs in an extremely thin film having a thickness of about 5 nm, and in a common bulk Ti film, a TiOx nanocrystal does not grow large. The phenomenon in which a TiOx nanocrystal in a modified Ti film grows large even at a relatively low temperature as compared with the melting point (1727° C.) of Ti was newly found by the present inventors. This structure is called a modified Pt—Ti—O gate structure and is distinguished from the structure in the related art (the above-described Pt—Ti—O gate structure in the related art).

However, the Pt film is composed of a plurality of Pt crystal grains, and the characteristic that Ti and oxygen (O) are present in a crystal grain boundary region existing among the plurality of Pt crystal grains and the characteristic that a TiOx nanocrystal is formed by oxidation of Ti flowing out from the Ti film at a Pt crystal grain boundary, particularly on a surface in the vicinity of a grain boundary triple point as the center do not change.

Therefore, various experiments were performed for a Si-MISFET having a modified Pt—Ti—O gate structure. As a result, the present inventors newly found that by additionally performing hydrogen annealing, extremely high speed response is achieved such that the rising response time is several seconds in a gas sensor.

Further, in the case of the modified Pt—Ti—O gate structure additionally subjected to hydrogen annealing, in the process of desorbing hydrogen from the gas sensor after stopping irradiation with hydrogen gas, a residual tail causing prolonged hydrogen response derived from a hydrogen trap having a delay time constant present in the modified Ti film or the $SiO_2$ film can be removed. This is considered to be an effect of the modified Pt—Ti—O gate structure in which the ratio of the oxygen-doped amorphous Ti in the modified Ti film is extremely reduced thereby reducing a hydrogen trap having a delay time constant.

Next, the basic structure of the Si-MISFET-type gas sensor having a modified Pt—Ti—O gate structure according to the first embodiment and experimental results will be described with reference to FIGS. 1 to 5.

FIG. 1 is an enlarged schematic cross-sectional view of a part of a gate structure of the Si-MISFET having a modified Pt—Ti—O gate structure according to the first embodiment.

On a Si layer 5, a gate insulating film 4 (e.g., a $SiO_2$ film) is formed, and on the gate insulating film 4, a modified TiOx film (a crystalline film composed of a TiOx nanocrystal (a TiOx microcrystal)) 1 is formed. Further, on the modified TiOx film 1, a Pt film (a gate electrode) is formed. This Pt film is composed of a plurality of Pt crystal grains 3, Ti and oxygen (O) are present in a crystal grain boundary gap 7 existing among the plurality of Pt crystal grains 3 (in FIG. 1, a portion where Ti and oxygen (O) are present is denoted by a reference numeral 2), and a TiOx nanocrystal 62 (a TiOx microcrystal) is formed at a Pt crystal grain boundary, particularly on a surface in the vicinity of a grain boundary triple point as the center (a modified Pt film). The modified TiOx film 1 also has an effect of maintaining adhesiveness between the gate insulating film 4 and the Pt film. In FIG. 1, a reference numeral 9 denotes a carrier inversion layer which depends on gate voltage.

Figure 2:
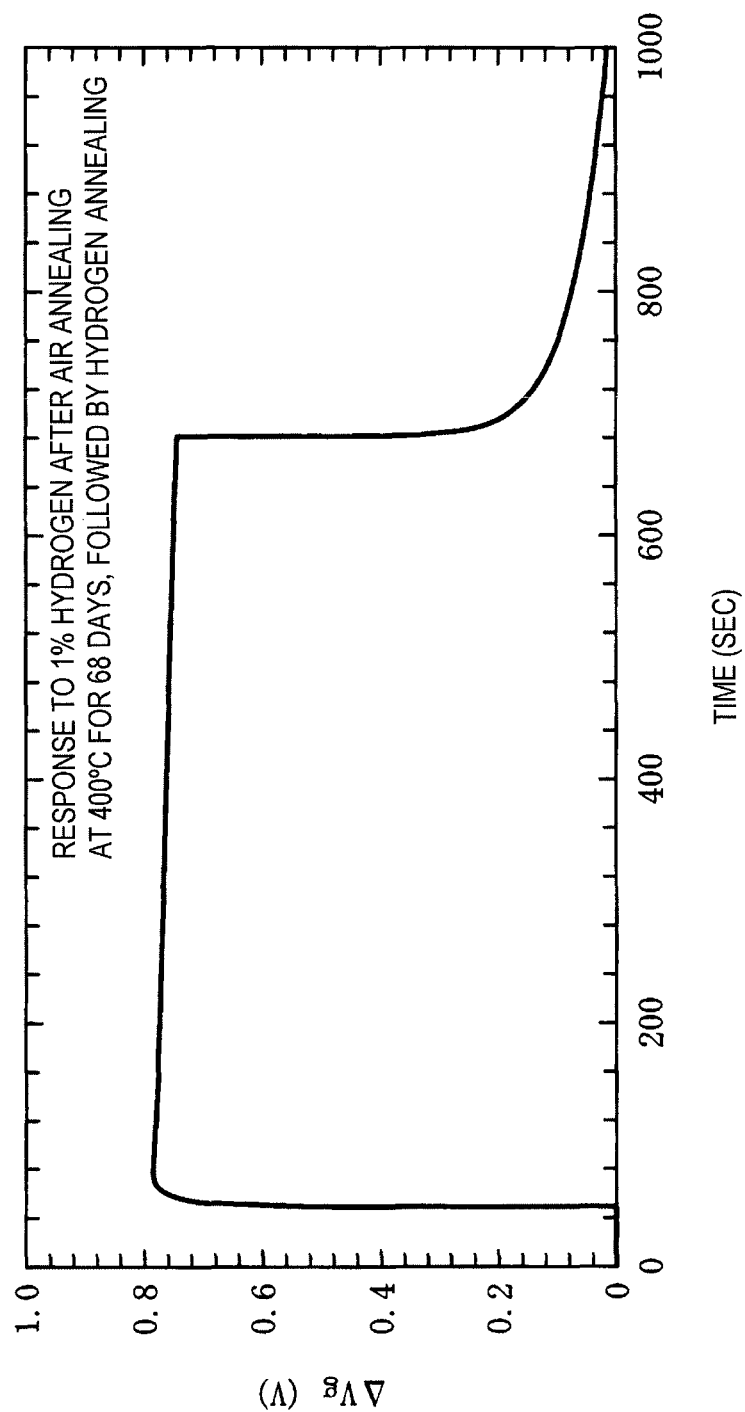
FIG. 2 is a graph for explaining a hydrogen response characteristic when the Si-MISFET having a Pt—Ti—O gate structure according to the first embodiment of the invention was annealed in an air atmosphere at 400° C. for 68 days, followed by hydrogen annealing, and thereafter the Si-MISFET was irradiated with 1% hydrogen diluted with air.

FIG. 2 is a graph for explaining a hydrogen response characteristic when the Si-MISFET having a Pt—Ti—O gate structure was annealed in an air atmosphere at 400° C. for 68 days, followed by hydrogen annealing, and thereafter the Si-MISFET was irradiated with 1% hydrogen diluted with air. In the graph, the vertical axis indicates a hydrogen response intensity (ΔVg). The thickness of the Pt film is 15 nm, the thickness of the Ti film is 5 nm, and the thickness of the $SiO_2$ film is 18 nm.

As shown in FIG. 2, the rising time was several seconds, the threshold voltage (Vth) was not shifted, and a residual response intensity (ΔVgres) was not generated.

In the first embodiment, the modified Pt—Ti—O gate structure was prepared by fixing the thickness of the Ti film at 5 nm and the thickness of the Pt film at 15 nm, and performing annealing in an air atmosphere at 400° C. for 68 days. However, in the practical point of view, it is preferred to perform annealing in a short time. Due to this, for example, a method for performing annealing in an oxygen atmosphere at 400° C. for 7 days, or for example, a method for performing annealing at 450° C. for 1 day may be adopted. By doing this, the modified Pt—Ti—O gate structure can be realized.

Although the modified Pt—Ti—O gate structure can be formed by continuing annealing in an oxygen atmosphere at a low temperature such as 300° C. for about 2 years, a temperature of about 300° C. is the lower limit temperature.

One point of the modified Pt—Ti—O gate structure is to use a structure in which a TiOx nanocrystal in the modified Ti film grows large to form a TiOx microcrystalline region, and an oxygen-doped amorphous Ti region is significantly reduced (a modified TiOx film). However, it is difficult to accurately control the ratios of the TiOx microcrystalline region and the oxygen-doped amorphous Ti region by a specific value such as an annealing temperature, a gas species in an oxygen atmosphere, or an annealing time. With respect to the response characteristic to hydrogen gas or another gas, substantially the same response characteristic is obtained if the TiOx microcrystalline region can be formed such that the ratio thereof is 50% or more in the modified TiOx film, and therefore, a film in which the TiOx microcrystalline region is contained at a ratio of 50% or more and 100% or less is defined as a modified TiOx film.

It goes without saying that a gas sensor can be formed by the same method even if a W (tungsten) film, a Mo (molybdenum) film, a Nb (niobium) film, a Ta (tantalum) film, a Cr (chromium) film, or a Sn (tin) film is used in place of the Ti film in the Si-MISFET-type gas sensor having a modified Pt—Ti—O gate structure described in the first embodiment.

Figure 3:
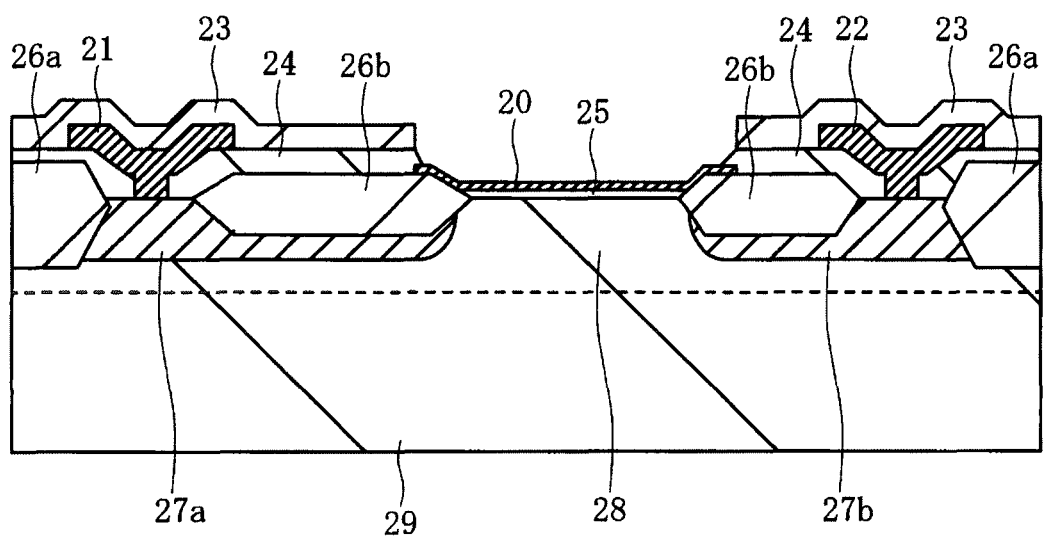
FIG. 3 is a cross-sectional view of a principal part of the Si-MISFET having a modified Pt—Ti—O gate structure according to the first embodiment of the invention.
Figure 4:
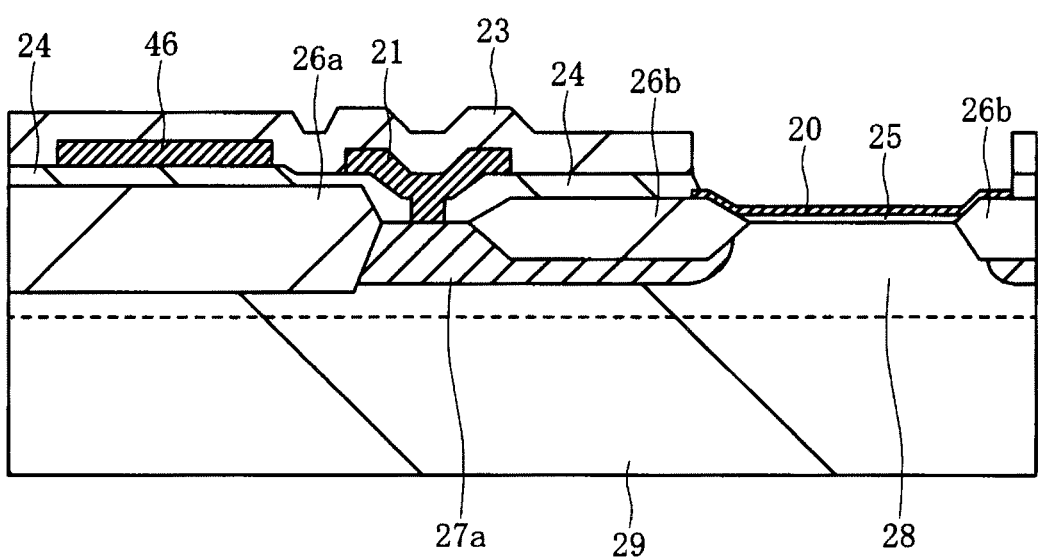
FIG. 4 is a cross-sectional view of a principal part of the Si-MISFET having a modified Pt—Ti—O gate structure according to the first embodiment of the invention.

Next, a method for producing a Si-MISFET having a modified Pt—Ti—O gate structure according to the first embodiment will be described with reference to FIGS. 3 and 4. FIGS. 3 and 4 are each a cross-sectional view of a principal part of the Si-MISFET having a modified Pt—Ti—O gate structure. Here, a process of producing a modified Pt—Ti—O gate structure which is a principal part of the Si-MISFET having a modified Pt—Ti—O gate structure according to the first embodiment and an annealing treatment in an atmosphere containing oxygen (O) will be mainly described.

The explanation will be made with an n-channel type MISFET in which the chip size is, for example, 2 mm×2 mm, the gate length (Lg) is 10 μm, and the gate width (Wg) is 150 μm.

First, as shown in FIG. 3, a p-type semiconductor layer (a p-type well) 28 is formed by introducing a p-type impurity into a semiconductor substrate 29, and then, locally oxidized films 26a and 26b are formed on the p-type semiconductor layer 28. The locally oxidized film 26b defines a gate electrode forming region, and therefore is formed from a $SiO_2$ film having a thickness of, for example, 250 nm by performing local oxidation. Subsequently, in order to form an n-type channel region on the surface of the p-type semiconductor layer 28, ion implantation of an impurity is performed at a dose of $10×10^{11}/cm^2$. Thereafter, ion implantation for forming an $n^+$-type semiconductor region which will become a source region 27a and a drain region 27b in the p-type semiconductor layer 28 is performed to form an active layer of a Si-MISFET.

Subsequently, a pretreatment is performed for the semiconductor substrate 29, and then, a gate insulating film 25 having a thickness of 18 nm is formed on the surface of the p-type semiconductor layer 28. This gate insulating film 25 is composed of, for example, a $SiO_2$ film, and can be formed by a thermal oxidation method in a water vapor atmosphere. Thereafter, for example, by a lift-off method, a Ti film (not shown in the drawing) and a gate electrode 20 composed of a Pt film are formed on the gate insulating film 25. The thickness of the Ti film is, for example, 5 nm, and the thickness of the Pt film is, for example, 15 nm.

At this time, as shown in FIG. 3, the n⁺-type semiconductor region which constitutes the source region 27a and the drain region 27b is formed in accordance with the locally oxidized film 26b that defines the forming region of the gate electrode 20. Then, the gate electrode 20 is formed such that it covers not only the gate insulating film 25, but also an edge of the locally oxidized film 26b, and is disposed such that an edge of the gate electrode 20 overlaps with the edge of the n⁺-type semiconductor region. This is because, in the first embodiment, a technique for forming an n⁺-type semiconductor region in a self-aligning manner with respect to the gate electrode 20, which is a primary method as a method for forming a Si-MISFET cannot be used. The Ti film and the Pt film constituting the gate electrode 20 are formed by, for example, an electron beam vapor deposition method.

Subsequently, by performing air annealing in a high-purity air atmosphere at a heat treatment temperature of 400° C. for a heat treatment period of 68 days, a gate structure which is a feature of the first embodiment shown in the above-described FIG. 1 can be realized.

Thereafter, on the semiconductor substrate 29 including on the gate electrode 20, an insulating film 24 composed of PSG (phosphorus-doped glass) is formed. Then, a contact hole that penetrates this insulating film 24 is formed, followed by a surface treatment or the like. The thickness of this insulating film 24 is, for example, 500 nm. Then, a source electrode 21 and a drain electrode 22, each of which is composed of an Al (aluminum) film containing Si, are formed on the insulating film 24 including the internal part of the contact hole. The thicknesses of the source electrode 21 and the drain electrode 22 are each, for example, 500 nm. A lead-out line connected to the gate electrode 20 is not shown in the drawing.

Further, as shown in FIG. 4, as a heater for heating a chip, a wiring 46 composed of an Al film containing Si, which is the same material as that of the source electrode 21 or the drain electrode 22, is formed. The width of this wiring 46 is, for example, 20 μm, and the length thereof is, for example, 29,000 μm.

Subsequently, hydrogen annealing is performed in a nitrogen atmosphere containing hydrogen at a concentration of 1% at a heat treatment temperature of 380° C. for a heat treatment time of 30 minutes.

Then, an insulating film 23 which functions as a passivation film is formed on the semiconductor substrate 29 such that it covers the source electrode 21, the drain electrode 22, and the wiring 46. This insulating film 23 is composed of, for example, a laminate film of PSG (phosphorus-doped glass) and a silicon nitride film. The silicon nitride film is formed by a low-temperature plasma CVD method, and the thickness thereof is, for example, 700 nm.

Finally, an opening is formed on an electrode pad (not shown in the drawing) for connecting to a bonding wire, and also another opening is formed such that the gate electrode 20 serving as a sensor section is exposed.

At this time, in the same chip, also a reference Si-MISFET, in which the insulating films 23 and 24 on the gate electrode 20 are not removed, that is, which does not respond to hydrogen, is formed at the same time in some cases. In this case, the threshold voltages (Vth) of the sensor Si-MISFET and the reference Si-MISFET are substantially the same since the same air annealing treatment and hydrogen annealing treatment were performed.

In the case of the first embodiment, when the threshold voltage (Vth) is defined as a gate voltage (Vg) which provides a drain current (Ids) of 10 μA under the condition that the drain voltage (Vds) is set to 1.5 V, and a short-circuit occurs between the source region 27a and the p-type semiconductor layer 28, the threshold voltage (Vth) was 1.1 V. Further, when a standard chip was mounted, the wiring resistance was 240Ω at a chip temperature of 115° C., and 280.5Ω at a chip temperature of 170° C. In this manner, by using the modified Pt—Ti—O gate structure, as shown in the above-described FIG. 2, a Si-MISFET-type gas sensor wherein the rising response time at the time of irradiation with hydrogen gas is several seconds, the threshold voltage (Vth) is not shifted, and a residual response intensity (ΔVgres) is not generated can be realized.

The modified Pt—Ti—O gate structure according to the first embodiment has an effect of removing a residual tail causing prolonged hydrogen response derived from a hydrogen trap having a delay time constant present in the modified Ti film or the SiO₂ film in the process of desorbing hydrogen from the gas sensor after stopping irradiation with hydrogen gas. This is an effect of the modified Pt—Ti—O gate structure according to the first embodiment in which the ratio of the oxygen-doped amorphous Ti in the modified Ti film is extremely reduced thereby reducing a hydrogen trap having a delay time constant.

In the above-described method for producing a Si-MISFET according to the first embodiment, as the gate insulating film, a SiO₂ film is used, however, a laminate film in which an insulating film such as a Ta₂O₅ (tantalum oxide) film, an Al₂O₃ (alumina) film, or a Si₃N₄ (silicon nitride) film is formed on a SiO₂ film may be used, and after forming this laminate film, in the same manner as the above-described production process, a Ti film and a gate electrode 20 composed of a Pt film are formed.

Further, in the above-described method for producing a Si-MISFET according to the first embodiment, in the production of the modified Pt—Ti—O gate structure, the thickness of the Ti film is fixed at 5 nm, the thickness of the Pt film is fixed at 15 nm, and annealing is performed in an air atmosphere, however, annealing may be performed in an oxygen (oxygen gas) atmosphere, an oxygen (oxygen gas) atmosphere diluted with Ar, or an oxygen (oxygen gas) atmosphere diluted with N (nitrogen).

Further, in the above-described method for producing a Si-MISFET according to the first embodiment, in the production of the modified Pt—Ti—O gate structure, the thickness of the Ti film is fixed at 5 nm, the thickness of the Pt film is fixed at 15 nm, and annealing is performed in an air atmosphere at a heat treatment temperature of 400° C. for 68 days, however, by performing annealing in an oxygen atmosphere, even if the heat treatment temperature is 400° C., the heat treatment time can be decreased to about 7 days.

Further, in the above-described method for producing a Si-MISFET according to the first embodiment, in the production of the modified Pt—Ti—O gate structure, the thickness of the Ti film is fixed at 5 nm, the thickness of the Pt film is fixed at 15 nm, and annealing is performed in an air atmosphere at a heat treatment temperature of 400° C. for 68 days, however, the annealing may be performed at a heat treatment temperature ranging from 350° C. to 500° C. For example, in the case where the heat treatment temperature is 500° C., the modified Pt—Ti—O gate structure shown in the above-described FIG. 1 can be formed for a heat treatment time of about 5 hours.

Further, in the above-described method for producing a Si-MISFET according to the first embodiment, a description is made of the method for producing a Si-MISFET by fixing the thickness of the Ti film at 5 nm and the thickness of the Pt film at 15 nm in the production of the modified Pt—Ti—O gate structure, however, the thicknesses of the Ti film and the Pt film are not limited thereto. For example, in the detection of hydrogen gas at a concentration of 0.1%, the thickness of the Ti film can be set to 10 nm or less and the thickness of the Pt film can be set to 30 nm or less. Further, for example, in the detection of hydrogen gas at a concentration of 50%, the upper limit of the thickness of the Pt film which can respond was about 90 nm. In this case, the thickness of the Ti film is 5 nm or more and the upper limit thereof is about 15 nm. For example, by setting the thickness of the Ti film to 30 nm and the thickness of the Pt film to 90 nm, and for example, performing annealing in an air atmosphere at a heat treatment temperature of 400° C. for about 200 hours, peeling of the Pt film is caused, and the film no longer responses to hydrogen gas.

In fact, in the detection of hydrogen gas at a concentration of 0.1%, as for the hydrogen response intensity ($\Delta Vg$), in the case where the thickness of the Ti film is as thin as 5 nm, the film responds to hydrogen gas when the thickness of the Pt film is up to 30 nm. However, in the case where the thickness of the Pt film is 45 nm, even if annealing is performed in an air atmosphere for 128 hours, the film does not respond to hydrogen gas. It has been reported that in the case where a Ti film is not present, when the thickness of a Pt film is up to about 90 nm, the film responds to hydrogen gas. Therefore, it is considered that an effect of insertion of a Ti film that inhibits sensor response is exhibited.

In order to understand this characteristic phenomenon, TEM observation and TEM-EDX analysis were performed for a sample (the thickness of a Pt film is 78 nm and the thickness of a Ti film is 32 nm) which was annealed in an air atmosphere at 400° C. for 128 hours. The result is shown in FIG. 5. The gate insulating film is a $SiO_2$ film, and the thickness thereof is 16 nm.

A portion where peeling occurred on the surface shown in FIG. 5 is found to be a Pt crystal grain block from the EDX analysis, and a second portion, a seventh portion, and an eighth portion (indicated by circles), which look dark, are each found to be a Pt microcrystal from the FET images (high-speed Fourier-transformed images) thereof. A first portion, a third portion, a fourth portion, a fifth portion, and a sixth portion (indicated by circles), which look white, are each titanium oxide. In particular, the film thicknesses of the first portion, the fourth portion, and the fifth portion are increased due to oxidation of Ti.

What is found from this TEM observation is that if the thickness of the Ti film is increased, due to oxygen (O) that invades from the Pt crystal grain boundary, the Ti film under the Pt crystal grain boundary expands and the Pt crystal grain block is peeled off in a given time. It is considered that after the Pt crystal grain is peeled off, the Ti film is rapidly oxidized. The entire laminate film of the Pt film and the Ti film is covered with the Pt film, and therefore, the threshold voltage (Vth) is controlled by the Pt film. However, it is presumed that if the oxidation of the Ti film further proceeds, a region which is covered with the Pt film is decreased, and the threshold voltage (Vth) is gradually decreased.

However, in the fourth portion, the fifth portion, the sixth portion, and the eighth portion, in the process of locally converting Ti to TiO, Pt (the eighth portion) invades into a lower portion of TiO (the fourth portion and the fifth portion), and in this portion, peeling occurs due to the invasion of Pt. A phenomenon in which peeling occurs due to the invasion of Pt as described above is a reconfirmed phenomenon, and it can be said that a combination of the thickness of the Pt film and the thickness of the Ti film which does not cause peeling is critically important.

If the heating temperature can be decreased and heating can be performed for a super long time, as shown in the above-described FIG. 5, even when the thickness of the Ti film is as thick as 32 nm, by extremely slowly invading oxygen from the Pt crystal grain boundary, the Ti film may be extremely slowly expanded to allow Ti to slowly flow out from the Pt crystal grain boundary. By doing this, there is a possibility that peeling of the Pt film due to the occurrence of stress accompanying the expansion of the Ti film will be suppressed. However, in consideration of a realistic heating time, in the detection of hydrogen gas at a concentration of 0.1%, the thickness of the Ti film is in a range of from 1 nm to 10 nm, and the thickness of the Pt film is in a range of from 1 nm to 30 nm. Further, the combination of the thickness of the Pt film and the thickness of the Ti film capable of detecting hydrogen gas at a concentration up to about 50% is such that the maximum thickness of the Pt film is about 90 nm, and the thickness of the Ti film is from about 3 nm to 15 nm at most.

It goes without saying that a gas sensor can be formed by the same method even if a W film, a Mo film, a Nb film, a Ta film, a Cr film, or a Sn film is used in place of the Ti film in the Si-MISFET-type gas sensor having a modified Pt—Ti—O gate structure described in the first embodiment.

In the first embodiment, after forming the wiring 46, hydrogen annealing is performed in a nitrogen atmosphere containing hydrogen at a concentration of 1% at a heat treatment temperature of 380° C. for a heat treatment time of 30 minutes. However, by performing deuterium annealing at a heat treatment temperature of 400° C. for a heat treatment time of 60 minutes using deuterium in place of hydrogen, desorption of hydrogen can be prevented at a temperature up to about 400° C. Further, an effect of deuterium annealing is as follows. Deuterium has a function of terminating a hydrogen trap in the vicinity of the gate insulating film also in the Si-MISFET-type gas sensor having a Pt—Ti—O gate structure in the related art shown in the above-described FIG. 12, and therefore, desorption of hydrogen can be prevented at a temperature up to about 400° C. Accordingly, a similar effect of achieving high-speed response and reducing a residual response intensity is exhibited. In general, hydrogen gas containing hydrogen at a concentration of from 0.1% to 3.5% or deuterium gas containing deuterium at a concentration of from 0.1% to 3.5% is used.

Second Embodiment

The modified Pt—Ti—O gate structure is stabilized by annealing at 400° C. over a long period of time of 68 days, and therefore, by applying the modified Pt—Ti—O gate structure to a SiC-MISFET gate electrode, stable operation can be achieved at a temperature of about 400° C. for a long period of time. A point that the modified Pt—Ti—O/$SiO_2$/SiC substrate structure adopting this gate structure is very stable is different from the Pt (100 nm)/$SiO_2$/SiC substrate structure ("Pt 100 nm" is described on the third line from the bottom of the left column in page 201 of the above-described NPL 4) in the related art.

In a production process of forming a SiC-MISFET-type gas sensor, after forming a gate insulating film (e.g., a $SiO_2$ film), hydrogen annealing is performed at 800° C. to 1000° C. for about 30 minutes, whereby hydrogen termination is performed in the vicinity of a $SiO_2$/SiC boundary surface. By doing this, a phenomenon in which terminating hydrogen starts to be desorbed (a phenomenon in which the rising response time at the time of gas irradiation is delayed to about several hundreds of seconds, the threshold voltage (Vth) is significantly shifted, and a residual response intensity (ΔVgres) is generated) can be prevented from occurring, and degeneration of the hydrogen response characteristic can be prevented.

Next, the basic structure of the SiC-MISFET-type gas sensor having a modified Pt—Ti—O gate structure according to the second embodiment will be described with reference to FIG. 6.

Figure 6:
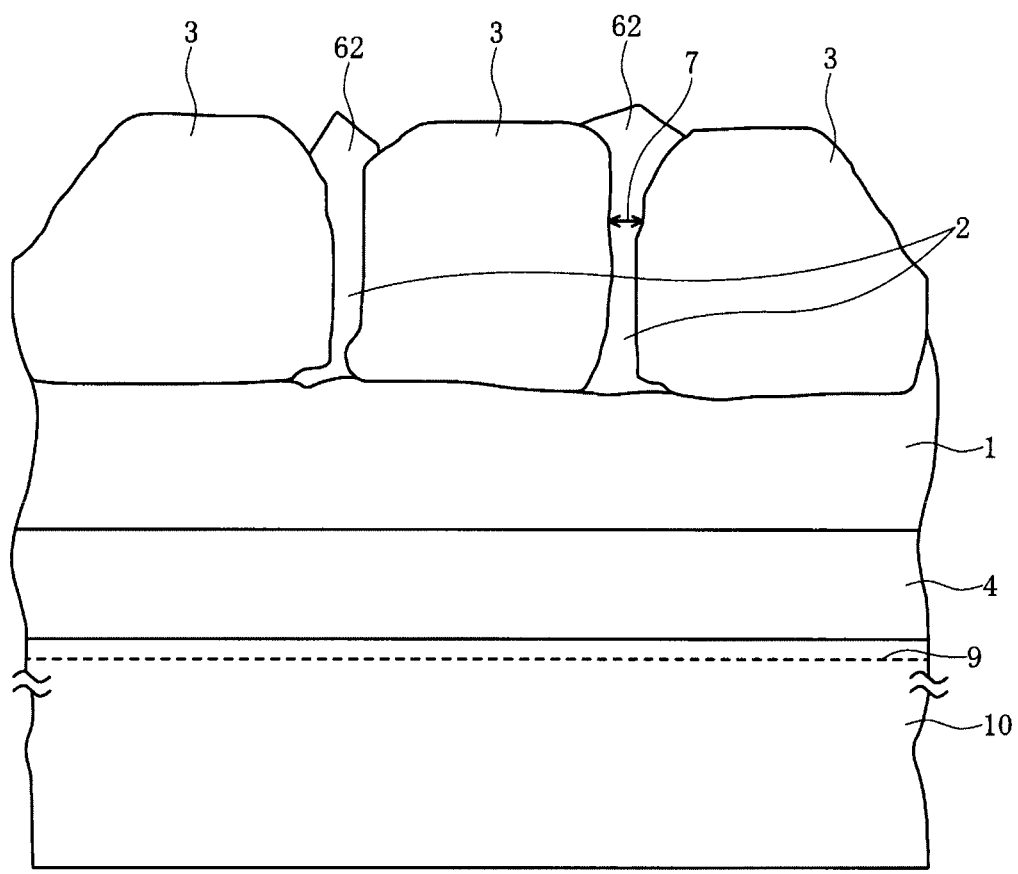
FIG. 6 is an enlarged schematic cross-sectional view of a part of a gate structure of a SiC-MISFET having a modified Pt—Ti—O gate structure according to a second embodiment of the invention.

FIG. 6 is an enlarged schematic cross-sectional view of a part of a gate structure of the SiC-MISFET having a modified Pt—Ti—O gate structure according to the second embodiment.

On a SiC layer 10, a gate insulating film (e.g., a $SiO_2$ film) 4 is formed, and on the gate insulating film 4, a modified TiOx film 1 is formed. Further, on the modified TiOx film 1, a Pt film (a gate electrode) is formed. This Pt film is composed of a plurality of Pt crystal grains 3, Ti and oxygen (O) are present in a crystal grain boundary gap 7 existing among the plurality of Pt crystal grains 3 (in FIG. 6, a portion where Ti and oxygen (O) are present is denoted by a reference numeral 2), and a TiOx nanocrystal 62 is formed particularly on a surface in the vicinity of a grain boundary triple point as the center (a modified Pt film). In FIG. 6, a reference numeral 9 denotes a carrier inversion layer which depends on gate voltage.

Figure 7:
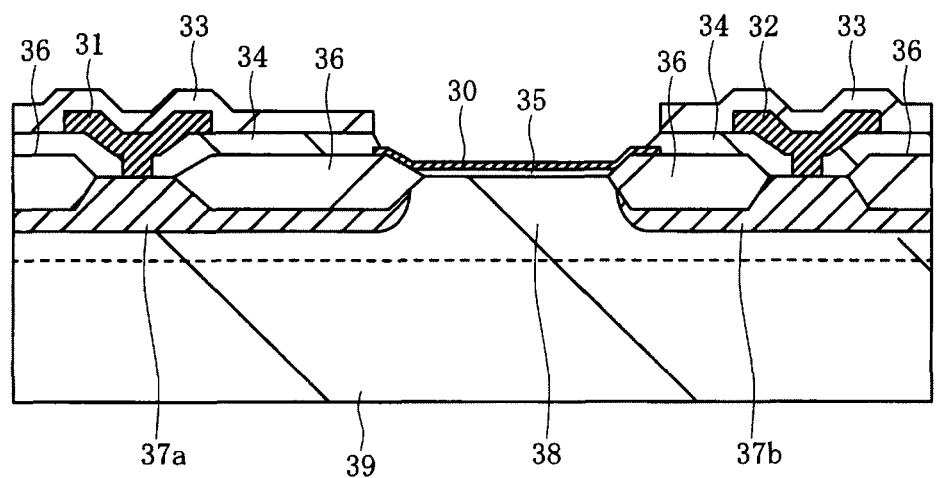
FIG. 7 is a cross-sectional view of a principal part of the SiC-MISFET having a modified Pt—Ti—O gate structure according to the second embodiment of the invention.
Figure 8:
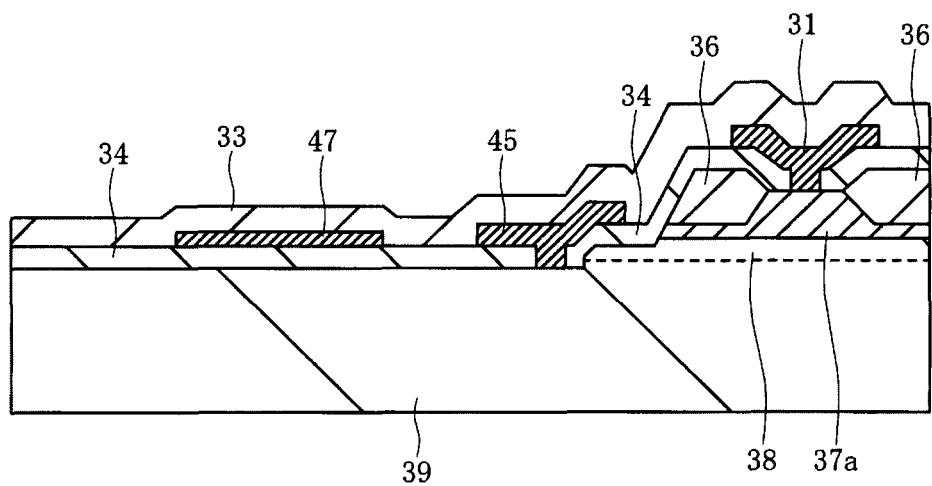
FIG. 8 is a cross-sectional view of a principal part of the SiC-MISFET having a modified Pt—Ti—O gate structure according to the second embodiment of the invention.

Next, a method for producing a SiC-MISFET-type gas sensor having a modified Pt—Ti—O gate structure according to the second embodiment will be described with reference to FIGS. 7 and 8. FIGS. 7 and 8 are each a cross-sectional view of a principal part of the SiC-MISFET having a modified Pt—Ti—O gate structure. Here, a process of producing a modified Pt—Ti—O gate structure which is a principal part of the SiC-MISFET having a modified Pt—Ti—O gate structure according to the second embodiment will be mainly described.

An n-channel type MISFET in which the gate length (Lg) is 20 μm and the gate width (Wg) is 300 μm was prepared.

First, as shown in FIG. 7, a p-type 4H—SiC 8° off semiconductor substrate 39 is prepared. On this semiconductor substrate 39, for example, a p-type semiconductor layer (a p-type well) 38 having a thickness of about 10 μm is formed by a homoepitaxial technique. The hole concentration in the p-type semiconductor layer 38 is, for example $7.5 \times 10^{15}/cm^3$. Subsequently, by using an oxidized film as a mask, ion implantation of an n-type impurity, for example, P (phosphorus) into the p-type semiconductor layer 38 is performed to form a source region 37a and a drain region 37b, in which the impurity concentration is $1 \times 10^{20}/cm^3$, and the depth from the surface of the p-type semiconductor layer 38 is about 200 nm. Subsequently, ion implantation of N (nitrogen) into the p-type semiconductor layer 38 is performed. The dosing energies are, for example, 2.5 keV and 5.5 keV, respectively, and the amounts of doses are, for example, each $10 \times 10^{11}/cm^2$. Thereafter, Ar annealing is performed in an Ar (argon) atmosphere at 1300° C. for 20 minutes.

Subsequently, a pretreatment is performed for the semiconductor substrate 39, and then, a gate insulating film 35 is formed on a part of the surface of the p-type semiconductor layer 38 by a wet oxidation method. This gate insulating film 35 is composed of, for example, a $SiO_2$ film, and has a thickness of, for example, 30 nm. In the wet oxidation method, for example, thermal oxidation at 850° C. for 30 minutes and thermal oxidation at 1100° C. for 6 hours are performed. By this wet oxidation method, also on the surface of the p-type semiconductor layer 38 of the source region 37a and the drain region 37b, a locally oxidized film 36 having a thickness of 60 nm is formed. In the source region 37a and the drain region 37b, the p-type semiconductor layer 38 in the vicinity of the surface thereof is in an amorphous state due to the ion implantation performed earlier, and therefore, a locally oxidized film 36 which is thicker than the gate insulating film 35 is formed by multiplication oxidation.

Subsequently, hydrogen annealing is performed in an Ar atmosphere (1% hydrogen diluted with Ar) in which hydrogen is diluted to a concentration of 1% at a heat treatment temperature of from 800° C. to 1000° C. for a heat treatment time of 30 minutes. At this time, if deuterium is used in place of hydrogen, an ability to maintain hydrogen termination is improved, which is the same as in the first embodiment. In general, hydrogen gas containing hydrogen at a concentration of from 0.1% to 3.5% is used.

Thereafter, for example, by a lift-off method, a Ti film (not shown in the drawing) and a gate electrode 30 composed of a Pt film are formed on the gate insulating film 35. The Ti film and the Pt film are continuously formed. The thickness of the Ti film is, for example, 5 nm, and the thickness of the Pt film is, for example, 15 nm.

At this time, as shown in FIG. 7, an $n^+$-type semiconductor region which constitutes the source region 37a and the drain region 37b is formed in accordance with the locally oxidized film 36 that defines the forming region of the gate electrode 30. Then, the gate electrode 30 is formed such that it covers not only the gate insulating film 35, but also an edge of the locally oxidized film 36, and is disposed such that an edge of the gate electrode 30 overlaps with the edge of the $n^+$-type semiconductor region. This is because, in the second embodiment, a technique for forming an $n^+$-type semiconductor region in a self-aligning manner with respect to the gate electrode 30, which is a primary method as a method for forming a SiC-MISFET cannot be used. The Ti film and the Pt film are formed by, for example, an electron beam vapor deposition method at a film forming speed of, for example, 10 nm/min.

Subsequently, by performing air annealing in high-purity air at a heat treatment temperature of 400° C. for a heat treatment period of 68 days, a gate structure which is a feature of the second embodiment shown in the above-described FIG. 6 can be realized. Here, hydrogen annealing can also be performed in a nitrogen atmosphere in which the concentration of hydrogen or deuterium is from about 0.1% to 3.5% at a heat treatment temperature of from about 400° C. to 630° C. for a heat treatment time of 30 minutes.

Thereafter, on the semiconductor substrate 39 including on the gate electrode 30, an insulating film 34 composed of PSG (phosphorus-doped glass) is formed. Then, a contact hole that penetrates this insulating film 34 is formed, followed by a surface treatment or the like. Then, a source electrode 31 and a drain electrode 32, each of which is composed of a laminate film obtained by sequentially depositing a Ti film, a Pt film, and a Mo film, are formed on the insulating film 34 including the internal part of the contact hole. The thicknesses of the source electrode 31 and the drain electrode 32 are each, for example, 500 nm. A lead-out line connected to the gate electrode 30 is not shown in the drawing.

Unlike the above-described first embodiment, as the semiconductor substrate 39, a p-type SiC is used. Due to this, it is necessary to fix the potential of the semiconductor substrate 39. There is a method for forming a substrate potential fixing electrode on the entire rear surface of the semiconductor substrate 39 by depositing a Ti film on the rear surface of the semiconductor substrate 39, and then forming a Pt film thereon, or the like, however, in the second embodiment, a substrate potential fixing electrode and a heater are formed on the front surface side of the semiconductor substrate 39.

As shown in FIG. 8, first, on the semiconductor substrate 39, for example, a p-type semiconductor layer (a p-type well) 38 having a thickness of about 10 μm is formed by a homoepitaxial technique. The hole concentration in the p-type semiconductor layer 38 is, for example $7.5 \times 10^{15}$/cm$^3$. Subsequently, the p-type semiconductor layer 38 is removed by mesa etching except for a region where a MISFET is formed (a region where a gate electrode, a source region, and a drain region are formed). Then, as described above, a substrate potential fixing electrode 45 is formed in accordance with the process of forming the source electrode 31 and the drain electrode 32.

As a heater for heating a chip, a wiring 47 composed of a laminate film obtained by sequentially depositing a Ti film, a Pt film, and a Mo film, which is the same material as that of the source electrode 31 or the drain electrode 32 is also formed. The width of this wiring 47 is, for example, 20 μm, and the length thereof is, for example, 29,000 μm.

Subsequently, hydrogen annealing is performed in a nitrogen atmosphere containing hydrogen at a concentration of 1% at a heat treatment temperature of 400° C. for a heat treatment time of 30 minutes.

Then, an insulating film 33 which functions as a passivation film is formed on the semiconductor substrate 39 such that it covers the source electrode 31, the drain electrode 32, the substrate potential fixing electrode 45, and the wiring 47. This insulating film 33 is composed of, for example, a laminate film of PSG (phosphorus-doped glass) and a silicon nitride film. The silicon nitride film is formed by a low-temperature plasma CVD method, and the thickness thereof is, for example, 700 nm.

Finally, an opening is formed on an electrode pad (not shown in the drawing) for connecting to a bonding wire, and an Au (gold) pad is formed such that it covers a bonding pad portion. The thickness of the Au pad is, for example, 500 nm. Incidentally, Au diffuses in Si even at a low temperature, and therefore, a laminate film in which a Pt film is deposited on a Ti film was used as a barrier metal between the source electrode 31 and the source region 37a, between the drain electrode 32 and the drain region 37b, and so on. At this time, when a heating treatment is performed, a Ti/Si alloy layer composed of Ti and Si is formed in the source electrode 31 or the drain electrode 32 depending on the heating condition. The Pt film functions as a diffusion barrier against Au into the Ti film or the Si film. By forming a TiSi$_2$ alloy film, an ohmic contact is stabilized.

Thereafter, an opening is formed such that the gate electrode 30 serving as a sensor section is exposed. At this time, in the same chip, also a reference SiC-MISFET, in which the insulating films 33 and 34 on the gate electrode 30 are not removed, that is, which does not respond to hydrogen, is formed at the same time in some cases. In this case, the threshold voltages (Vth) of the sensor SiC-MISFET and the reference SiC-MISFET are substantially the same since the same air annealing treatment and hydrogen annealing treatment were performed.

In the case of the second embodiment, when the threshold voltage (Vth) is defined as a gate voltage (Vg) which provides a drain current (Ids) of 10 μA under the condition that the drain voltage (Vds) is set to 5.0 V, and a short-circuit occurs between the source region 37a and the p-type semiconductor layer 38, the threshold voltage (Vth) was 2.0 V.

Further, when a standard chip was mounted, the wiring resistance was 240Ω at a chip temperature of 400° C.

Figure 9:
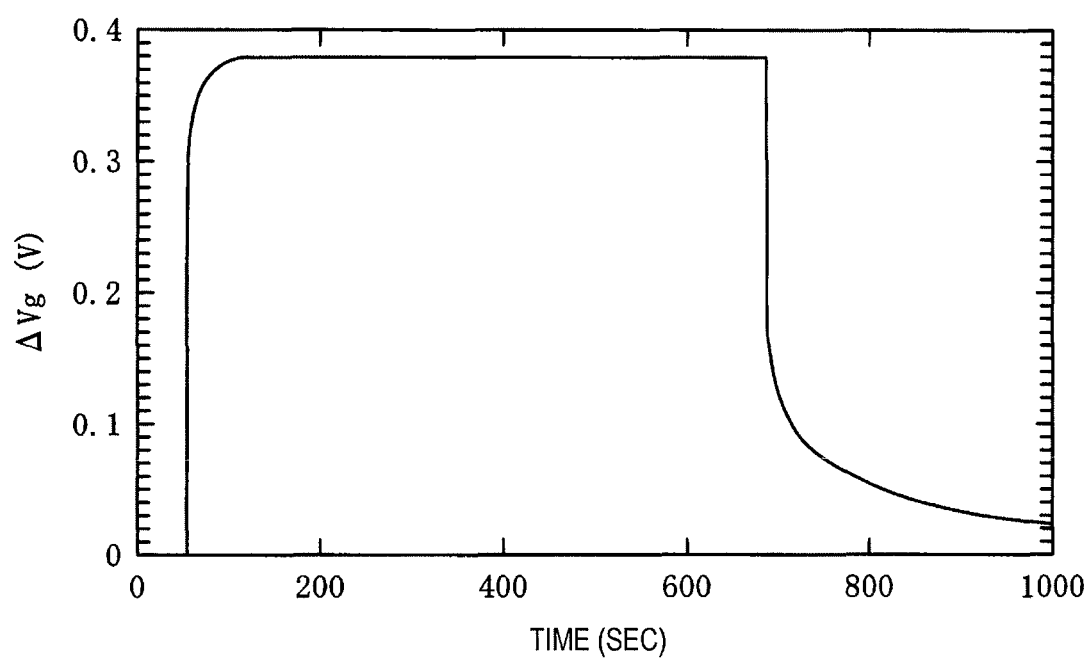
FIG. 9 is a graph for explaining a hydrogen response characteristic when the SiC-MISFET having a modified Pt—Ti—O gate structure according to the second embodiment of the invention was irradiated with 1% hydrogen diluted with air.

FIG. 9 is a graph for explaining a hydrogen response characteristic when the SiC-MISFET having a modified Pt—Ti—O gate structure was annealed in an air atmosphere at 400° C. for 68 days, followed by hydrogen annealing, and thereafter the SiC-MISFET was irradiated with 1%, hydrogen diluted with air. The operation temperature of the sensor is 400° C.

In this manner, by using the modified Pt—Ti—O gate structure, the rising response time at the time of irradiation with hydrogen gas is several seconds, the threshold voltage (Vth) is not shifted, and a residual response intensity (ΔVgres) is not generated. This is because desorption of terminating hydrogen in the vicinity of the boundary surface between the gate insulating film and the SiC semiconductor can be prevented by hydrogen annealing in an Ar atmosphere (1% hydrogen diluted with Ar) in which hydrogen is diluted to a concentration of 1%; at a heat treatment temperature of from 800° C. to 1000° C. for a heat treatment time of about 30 minutes.

In the above-described method for producing a SiC-MISFET according to the second embodiment, as the gate insulating film, a SiO$_2$ film is used, however, a laminate film in which an insulating film such as a Ta$_2$O$_5$ (tantalum oxide) film, an Al$_2$O$_3$ (alumina) film, or a Si$_3$N$_4$ (silicon nitride) film is formed on a SiO$_2$ film may be used, and after forming this laminate film, in the same manner as the above-described production process, a Ti film and a gate electrode 30 composed of a Pt film are formed.

Further, in the above-described method for producing a SiC-MISFET according to the second embodiment, in the production of the modified Pt—Ti—O gate structure, the thickness of the Ti film is fixed at 5 nm, the thickness of the Pt film is fixed at 15 nm, and annealing is performed in an air atmosphere at a heat treatment temperature of 400° C. for 68 days, however, the annealing may be performed at a heat treatment temperature ranging from 350° C. to 630° C. For example, in the case where the heat treatment temperature is 500° C., the modified Pt—Ti—O gate structure shown in the above-described FIG. 6 can be formed for a heat treatment time of about 5 hours.

Further, in the same manner as the above-described first embodiment, a description is made of the method for producing a SiC-MISFET by fixing the thickness of the Ti film at 5 nm and the thickness of the Pt film at 15 nm in the production of the modified Pt—Ti—O gate structure, however, the thicknesses of the Ti film and the Pt film are not limited thereto. For example, in the detection of hydrogen gas at a concentration of 0.1%, the thickness of the Ti film can be set to 10 nm or less and the thickness of the Pt film can be set to 30 nm or less. Further for example, in the detection of hydrogen gas at a concentration of 50%, the upper limit of the thickness of the Pt film which can respond can be set to about 90 nm.

In the case where a wiring composed of Al is used in the heater, when annealing is performed in an air atmosphere at a temperature of 475° C. or higher for several days, cracking occurs in a silicon nitride film serving as a final passivation film (an insulating film 33). This is because Al has a low melting point of 659° C. and has a coefficient of volume expansion of $3 \times 23.9 \times 10^{-6}$/° C. (20° C.), which is about 3 to 7 times higher than those of other metals. Therefore, in the case of using the wiring at a high temperature, as in the second embodiment, it is necessary to use a metal having a relatively high melting point and having a small coefficient of volume expansion such as Mo/Pt/Ti (a laminate film in which a Ti film, a Pt film, and a Mo film are sequentially deposited). Although the coefficient of volume expansion is generally increased with an increase in the temperature, a ratio of the coefficient of volume expansion between metal substances is not changed that much, and therefore, a comparison was made with values obtained at 20° C. When the heat treatment temperature is 630° C. or lower, the selection of the example (Mo/Pt/Ti) shown in the second embodiment can be adopted, however, when the heat treatment temperature is increased to as high as 930° C., it is necessary to use a wiring and a passivation film shown in the third embodiment described below.

Here, when a thermally oxidized film is formed on the surface of SiC, even if the SiC-MISFET-type gas sensor is operated at a temperature of 450° C. or higher, the gas sensor has sufficient resistance to environmental gas except for the case where an acidic gas is mixed in water vapor, etc. Accordingly, a SiC-MISFET-type gas sensor in which a silicon nitride film is not used as a passivation film can also be exemplified. This structure is, for example, a structure in which the silicon nitride film (the insulating film 33) is not formed in FIGS. 7 and 8. However, even if PSG (the insulating film 34) is directly deposited on the surface of SiC, a favorable passivation film is not formed only from PSG, and therefore, in a portion where PSG is directly contacted with SiC, an oxidized film (e.g., a $SiO_2$ film) is formed between PSG and SiC. This oxidized film is formed by thermal oxidation of the surface of SiC.

Third Embodiment

In the above-described second embodiment, as the gate electrode of the SiC-MISFET, a modified Pt—Ti—O gate structure is applied, and therefore, the operation temperature capable of ensuring reliability is up to 630° C. In order to ensure a temperature higher than 630° C., for example, a temperature up to 930° C. as the operation temperature capable of ensuring reliability, a modified Ir—Ti—O gate structure is needed. A gate portion and a heater wiring portion are different from those in the above-described second embodiment, and therefore, different points from the above-described second embodiment will be mainly explained.

The basic structure of the SiC-MISFET-type gas sensor having a modified Ir—Ti—O gate structure according to the third embodiment will be described with reference to FIGS. 10 to 11B.

Figure 10:
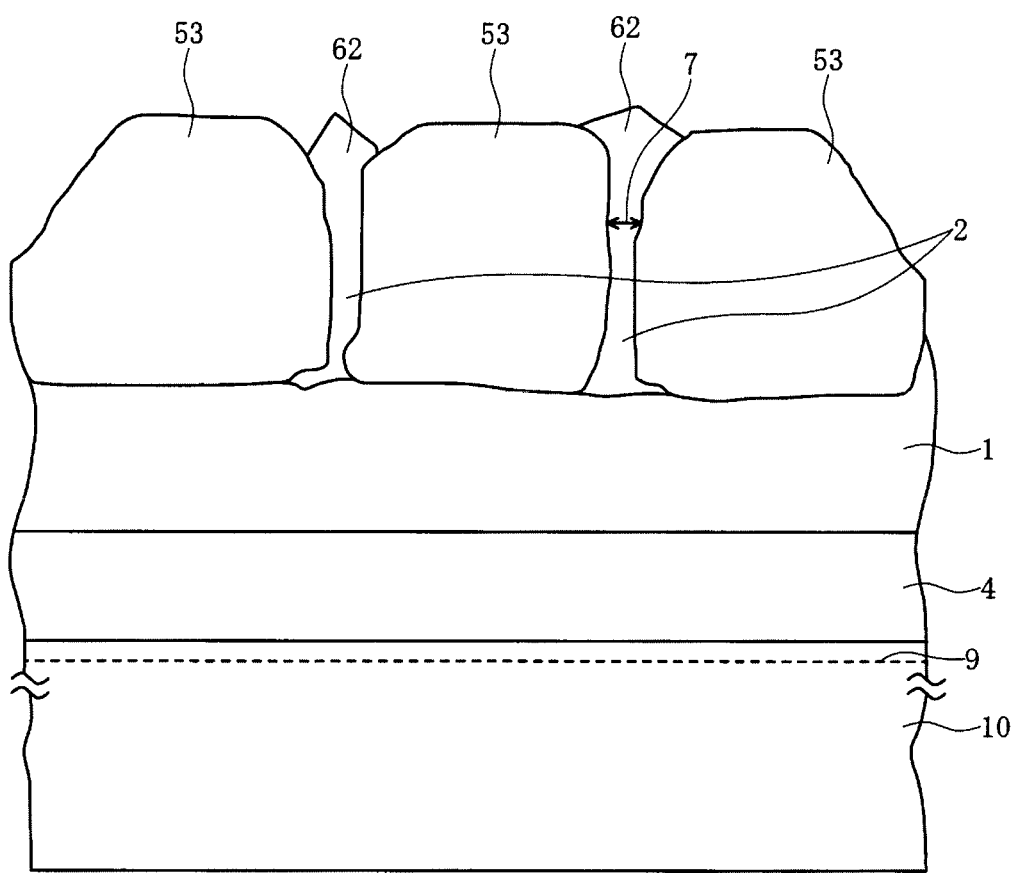
FIG. 10 is an enlarged schematic cross-sectional view of a part of a gate structure of a SiC-MISFET having a modified Ir—Ti—O gate structure according to a third embodiment of the invention.
Figure 11A:
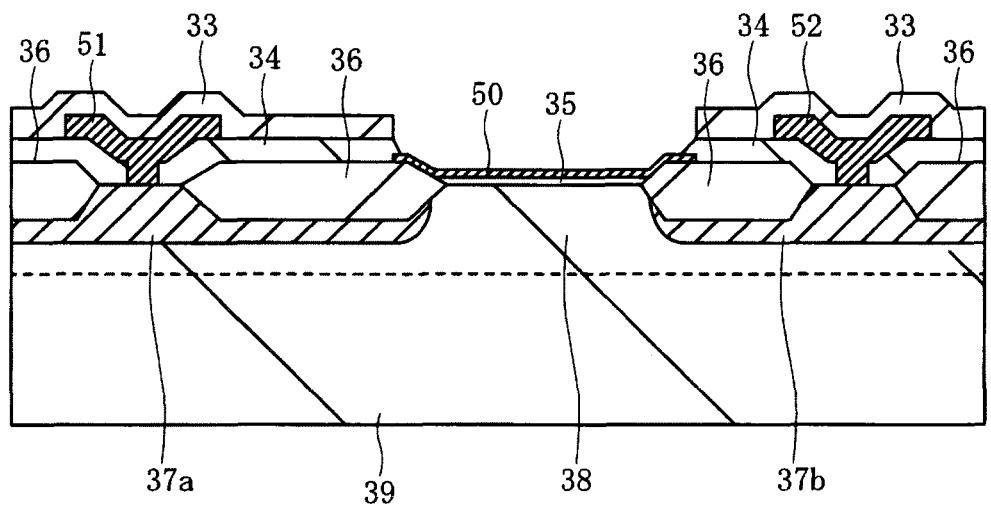
FIGS. 11A and 11B are each a cross-sectional view of a principal part of the SiC-MISFET having a modified Ir—Ti—O gate structure according to the third embodiment of the invention.
Figure 11B:
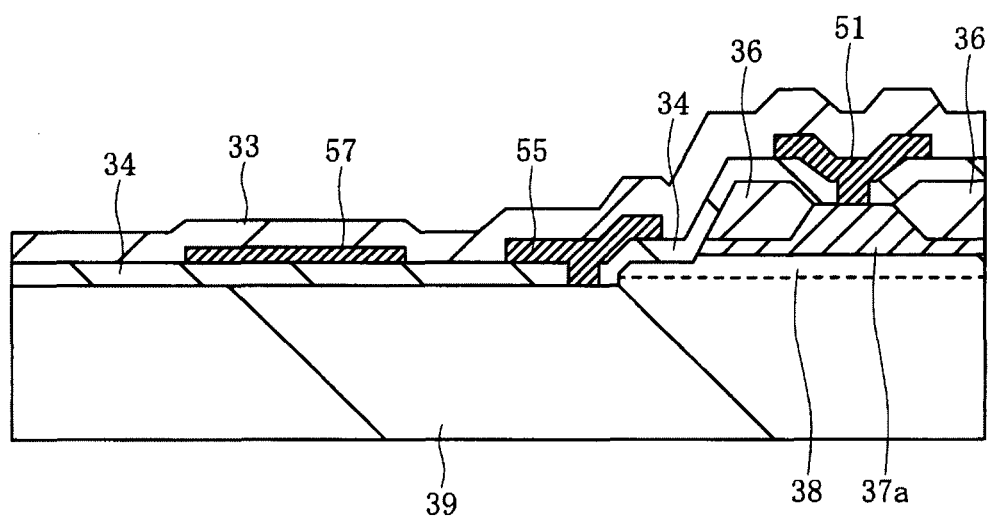

FIG. 10 is an enlarged schematic cross-sectional view of a part of a gate structure of the SiC-MISFET having a modified Ir—Ti—O gate structure according to the third embodiment, and FIGS. 11A and 11B are each a cross-sectional view of a principal part of the SiC-MISFET having a modified Ir—Ti—O gate structure. In FIG. 10, a reference numeral 53 denotes an Ir crystal grain, and the thickness of an Ir film is about 15 nm. Further, a gate electrode 50, a source electrode 51, and a drain electrode 52 shown in FIG. 11A, and a source electrode 51, a substrate potential fixing electrode 55, and a heater wiring 57 shown in FIG. 11B are different from those in the above-described second embodiment, and therefore will be described in detail below.

As shown in FIG. 10, the modified Ir—Ti—O gate structure can be realized by forming a Ti film having a thickness of 5 nm and an Ir film having a thickness of 15 nm by, for example, an EB method or the like on a gate insulating film (a $SiO_2$ film) 4, thereafter performing annealing in high-purity air at 500° C. for 2 hours (initial annealing), and further performing annealing in high-purity air at 630° C. for about 2 days. In order to reduce the treatment time, the heat treatment temperature may be raised from 630° C. to 800° C., and it is also possible to realize the modified Ir—Ti—O gate structure by annealing for several hours.

In the modified Ir—Ti—O gate structure formed by annealing at 630° C. for 2 days, as for the ratios of the TiOx microcrystalline region and the oxygen-doped amorphous Ti region, it can be determined from the TEM observation that the ratio of the TiOx microcrystalline region is about 70%. The reason why the ratio of the TiOx microcrystalline region changed as compared with the above-described modified Pt—Ti—O gate structure is considered that, other than the point that the heat treatment temperature and the heat treatment time are different, in the case of Ir, the speed and amount of oxygen (O) and Ti passing through the crystal grain boundary are different as compared with the case of Pt.

In the actual process, in the same manner as the second embodiment described above, by a lift-off method, a Ti film and a gate electrode 50 composed of an Ir film are formed on the gate insulating film 35. The Ti film and the Ir film are continuously formed. The thickness of the Ti film is from 1 nm to 15 nm, and the thickness of the Ir film is from 1 nm to 90 nm, and for example, the thickness of the Ti film is set to 5 nm, and the thickness of the Ir film is set to 15 nm. The condition for annealing in an oxygen atmosphere is as described above. In place of the Ti film, a film of a metal having a high melting point such as a W film or a Ta film may be used. In this case, in the initial annealing treatment, annealing is performed in high-purity air at 600° C. for 2 hours.

One of the reasons why the modified Ir—Ti—O gate structure is used is that since the structure aims at stable operation at a high temperature of from 600° C. to 900° C., a metal capable of providing a source electrode, a drain electrode, a substrate potential fixing electrode, and a heater wiring, each of which is stable at a high temperature, and a metal which has a small coefficient of volume expansion and high heat resistance so as not to cause breakage such as cracking in a passivation film accompanying thermal expansion are required.

In the above-describe second embodiment, a metal having a relatively high melting point and having a small coefficient of volume expansion such as Mo/Pt/Ti (a laminate film in which a Ti film, a Pt film, and a Mo film are sequentially deposited) is used, however, when the heat treatment temperature is increased to as high as 930° C., it is necessary to use a metal having high heat resistance such as W, W/Mo, or Mo/W/Mo. For example, the coefficients of volume expansion of W and Mo are $3 \times 3.3 \times 10^{-6}/°$ C. (20° C.) and $3 \times 8.9 \times 10^{-6}/°$ C. (20° C.), respectively, and such a metal can prevent the occurrence of breakage such as cracking in a passivation film accompanying thermal expansion. Further, even when such a metal having high heat resistance is used in a source electrode, a drain electrode, or a substrate potential fixing electrode, by laying Mo under W, molybdenum silicide is formed in a high-temperature treatment, and the respective electrodes can form a favorable ohmic contact with SiC. W has a high melting point of 3782° C., and therefore is stable at a high temperature. In addition, Mo has a melting point of 2622° C., which is higher than the melting point of Ti (1727° C.), and therefore is suitable for a stable operation at a high temperature such as 930° C. The heater wiring is designed to have 240Ω at 930° C. Since the operation temperature is as high as 930° C., a pad made of Au or the like is not formed in many cases.

As the gate insulating film, a $SiO_2$ film is used, however, a laminate film in which an insulating film such as a $Ta_2O_5$ (tantalum oxide) film, an $Al_2O_3$ (alumina) film, or a $Si_3N_4$ (silicon nitride) film is formed on a $SiO_2$ film may be used.

Also according to the above-described second and third embodiments, in the SiC semiconductor, by performing hydrogen annealing at a heat treatment temperature of from 800° C. to 1000° C. for a heat treatment time of 30 minutes after forming the gate insulating film (the $SiO_2$ film), it becomes possible to prevent desorption of hydrogen even in an operation at a high temperature up to about 600° C., and also the hydrogen response rising time can be maintained at several seconds. In general, hydrogen gas containing hydrogen at a concentration of from 0.1% to 3.5% is used.

Further, as a common means in the embodiments of the invention, deuterium annealing may be performed in place of hydrogen annealing. By allowing deuterium whose mass is about twice as much as that of hydrogen to compensate for a hydrogen trap site, desorption of hydrogen at a high temperature can be prevented in a wider temperature range as compared with the case of hydrogen annealing, and therefore, a semiconductor gas sensor which can be operated without deteriorating the rising response speed can be provided. In the SiC semiconductor, by performing deuterium annealing at a high temperature, it becomes possible to prevent desorption of hydrogen at a temperature up to about 900° C., and also the hydrogen response rising time can be maintained at several seconds.

Deuterium has one proton and one neutron in its nucleus, and therefore its mass is about twice as much as that of hydrogen. Accordingly, in the case of moving deuterium which terminates a hydrogen trap by thermal energy, an average speed is decreased to $1/\sqrt{2}$ as compared with the case of moving hydrogen according to the statistical mechanical theory. Therefore, although hydrogen is retained in a trap in hydrogen annealing at 600° C. (873 K), deuterium is expected to be retained in a trap at a temperature up to about 962° C. (1235 K=873 K×$\sqrt{2}$), which coincides with the above value.

Fourth Embodiment

In the above-described first, second and third embodiments, a Ti film is used as the crystalline film to be inserted between the gate insulating film and the Pt film, however, a W film, a Mo film, a Nb film, a Ta film, a Cr film, or a Sn film may be used, and the same effect as the Ti film can be obtained. However, as for the oxidation process after a film is formed by an electron beam vapor deposition method, it is not necessary to largely change the oxidation process of the Ti film in the case of a Mo film or a Cr film, however, in the case of a W film or a Ta film, it is necessary to perform oxidation at a higher temperature or, even at the same temperature, for a longer time as compared with the case of the Ti film. In addition, in the case of a Sn film, oxidation can be achieved at a lower temperature, or even at the same temperature, for a shorter time as compared with the case of the Ti film, and the same structure as the modified Pt—Ti—O structure can be realized.

For example, in the gate structure shown in the above-described FIG. 3 or 7, in the case where the thickness of a Sn film is 5 nm and the thickness of a Pt film is 15 nm, annealing in an air atmosphere may be performed at a heat treatment temperature of 300° C. for a heat treatment time of about 24 hours, and a modified Pt—Sn—O gate structure, in which the Ti film is replaced with the Sn film, can be realized. Since the melting point of the Sn film is as low as 232° C., a heat treatment temperature of 300° C. is sufficient.

However, once Sn is converted to an oxide ($SnO_2$), since the resulting oxide ($SnO_2$) is the most stable material in the field of gas sensor, a modified Pt—Sn—O gate structure is also converted to astable structure. On the other hand, in the case of a W film or a Ta film, the melting points of the W film and the Ta film are 3782° C. and 3029° C., respectively, and therefore, it is necessary to perform the initial annealing at a heat treatment temperature of around 600° C. As for the procedure for producing a modified Pt—W—0 gate structure, a modified Pt—Ta—O gate structure, a modified Ir—W—O gate structure, or a modified Ir—Ta—O gate structure, the basic structure (FIGS. 1, 6, 10, etc.) can be realized as shown in the third embodiment described above although the annealing temperature slightly varies. Also in this case, the annealing condition varies depending on an interrelationship between a Pt film or an Ir film and a W film, a Mo film, a Nb film, a Ta film, a Cr film, or a Sn film, which is the same as in the above-described first, second and third embodiments.

(Regarding Effects of Gas Sensors According to the Embodiments of the Present Invention)

Main effects obtained according to the embodiments of the present invention will be summarized below.

(1) By applying a modified Pt—Ti—O gate structure to a gate structure of a Si-MISFET, a semiconductor gas sensor which has an extremely high rising response speed and also exhibits a short residual response time when stopping gas irradiation can be provided.

(2) By applying a modified Pt—Ti—O gate structure to a gate structure of a SiC-MISFET, a semiconductor gas sensor which can be operated in a high-temperature environment ranging from about 250° C. to 630° C. can be provided.

(3) By applying a modified Ir—Ti—O gate structure to a gate structure of a SiC-MISFET, a semiconductor gas sensor which can be operated in a high-temperature environment ranging from about 250° C. to 930° C. can be provided.

(4) By performing hydrogen annealing at a temperature of from 800° C. to 1000° C. before forming a modified Pt—Ti—O gate structure of a SiC-MISFET, desorption of terminating hydrogen in the vicinity of a boundary surface between a gate insulating film and a SiC semiconductor can be prevented at the time of operation in a high-temperature environment ranging from about 300° C. to 630° C. Accordingly, a semiconductor gas sensor capable of preventing deterioration of the hydrogen response characteristic such as the occurrence of a phenomenon in which the rising response time at the time of gas irradiation is delayed to about several hundreds of seconds, the threshold voltage (Vth) is significantly shifted, and a residual response intensity ($\Delta$Vgres) is generated can be provided.

(5) By performing deuterium annealing at a temperature of from 800° C. to 1000° C. before forming a modified Ir—Ti—O gate structure of a SiC-MISFET-type gas sensor, desorption of terminating hydrogen in the vicinity of a boundary surface between a gate insulating film and a SiC semiconductor can be prevented at the time of operation in a high-temperature environment ranging from about 630° C. to 930° C. Accordingly, a semiconductor gas sensor capable of preventing deterioration of the hydrogen response characteristic such as the occurrence of a phenomenon in which the rising response time at the time of gas irradiation is delayed to about several hundreds of seconds, the threshold voltage (Vth) is significantly shifted, and a residual response intensity ($\Delta$Vgres) is generated can be provided.

(6) Also in a Si-MISFET-type gas sensor having a Pt—Ti—O gate structure, by performing deuterium annealing, desorption of terminating hydrogen in the vicinity of a boundary surface between a gate insulating film and a SiC semiconductor can be prevented. Accordingly, a semiconductor gas sensor capable of preventing deterioration of the hydrogen response characteristic such as the occurrence of a phenomenon in which the rising response time at the time of gas irradiation is delayed to about several hundreds of seconds, the threshold voltage (Vth) is significantly shifted, and a residual response intensity (ΔVgres) is generated can be provided.

The present inventors also examined a MISFET using a noble metal catalyst such as Pt as a gate metal after forming a metal oxide such as $TiO_2$ on a gate insulating film (e.g., a $SiO_2$ film). However, peeling of the noble metal catalyst such as Pt still easily occurs, accumulation of Ti or oxygen (O) at the crystal grain boundary of the noble metal catalyst such as Pt is not realized, and even when it is heated, a metal oxide such as $TiO_2$ cannot be decomposed unless the temperature is increased to high, however, when the temperature is increased to high, peeling of the noble metal catalyst such as Pt occurs. Accordingly, the above-described gate structure is not practical for use, and also this structure is largely different from the gate structure according to the present invention. That is, it means that the bonding between the modified Pt film and the modified TiOx film (or the modified Ti film) forms a stable film.

Hereinabove, the present invention accomplished by the present inventors have been described in detail with reference to the embodiments, however, it goes without saying that the present invention is not limited to the above-described embodiments, and can be modified variously within a range that does not depart from the gist of the present invention.

For example, in the above-described embodiments, the case where the present invention is applied to a MISFET-type gas sensor is described, however, it can also applied to a gas sensor including a capacitive element. In the gas sensor including a capacitive element, for example, a capacitive insulating film (e.g., a $SiO_2$ film) is formed on a Si layer (or a SiC layer), and a modified TiOx film is formed on the capacitive insulating film. Further, on the modified TiOx film, a Pt film constituting a gate electrode is formed. This Pt film is composed of a plurality of Pt crystal grains, and in a crystal grain boundary gap existing among the plurality of Pt crystal grains, Ti and oxygen (O) are present, and a TiOx nanocrystal is formed at a Pt crystal grain boundary, particularly on a surface in the vicinity of a grain boundary triple point as the center. Then, the above-described capacitive element is formed from a source electrode formed by adhering to the Si layer (or the SiC layer), the capacitive insulating film, and the gate electrode.

Further, in the above-described embodiments, an embodiment in which a modified Pt—Ti—O gate structure according to the present invention is applied to a MISFET-type gas sensor is described, however, the modified Pt—Ti—O gate structure can also be applied to a MIS-type CV (capacitive) element or a rectifying electrode of a Schottky diode. Further, it is apparent from the embodiments described above that in the above-described element, an Ir film can be used in place of the Pt film.

The present invention can be applied particularly to a semiconductor gas sensor and a method for producing the same.

What is claimed is:

1. A semiconductor gas sensor, comprising:
   (a) a semiconductor layer;
   (b) a gate insulating film formed on the semiconductor layer;
   (c) a crystalline film formed on the gate insulating film;
   (d) a gate electrode formed on the crystalline film;
   (e) a source region formed on the semiconductor layer;
   (f) a drain region formed on the semiconductor layer; and
   (g) a plurality of grain boundary regions, wherein
      the crystalline film is composed of modified TiOx, the modified TiOx being formed from a TiOx microcrystalline region and an oxygen-doped amorphous Ti region, and the ratio of the TiOx microcrystalline region is 50% or more,
      the gate electrode has a platinum film or an iridium film, the platinum film or the iridium film is composed of a plurality of crystal grains, and
      at least one grain boundary region includes oxygen and titanium and is disposed between immediately adjacent crystal grains, the at least one grain boundary region preventing the formation of a gap between the immediately adjacent crystal grains.

2. The semiconductor gas sensor according to claim 1, wherein the semiconductor layer is composed of silicon or silicon carbide, and the gate insulating film is composed of silicon oxide.

3. The semiconductor gas sensor according to claim 1, wherein the platinum film or the iridium film has a thickness of 1 nm or more and 90 nm or less, and the crystalline film has a thickness of 1 nm or more and 15 nm or less.

4. The semiconductor gas sensor according to claim 1, further comprising:
   (g) a heater for heating the semiconductor gas sensor, wherein
   the heater is composed of a laminate film in which a titanium film, a platinum film, and a molybdenum film are formed sequentially, a tungsten monolayer film, a laminate film in which a molybdenum film and a tungsten film are formed sequentially, or a laminate film in which a molybdenum film, a tungsten film, and a molybdenum film are formed sequentially.

5. A semiconductor gas sensor, comprising:
   (a) a semiconductor layer;
   (b) a gate insulating film formed on the semiconductor layer;
   (c) a crystalline film formed on the gate insulating film;
   (d) a gate electrode formed on the crystalline film;
   (e) a source region formed on the semiconductor layer;
   (f) a drain region formed on the semiconductor layer; and
   (g) a plurality of grain boundary regions, wherein
      the crystalline film is composed of modified metal oxide, the modified metal oxide being formed from a metal oxide microcrystalline region and an oxygen-doped amorphous metal region, and the ratio of the metal oxide microcrystalline region is 50% or more,
      the gate electrode has a platinum film or an iridium film, the platinum film or the iridium film is composed of a plurality of crystal grains, and
      the metal is tungsten, molybdenum, tantalum, niobium, chromium, or tin, and
      at least one grain boundary region includes oxygen and titanium and is disposed between immediately adjacent crystal grains, the at least one grain boundary region preventing the formation of a gap between the immediately adjacent crystal grains.

6. The semiconductor gas sensor according to claim 5, wherein the semiconductor layer is composed of silicon or silicon carbide, and the gate insulating film is composed of silicon oxide.

7. The semiconductor gas sensor according to claim 5, wherein the platinum film or the iridium film has a thickness of 1 nm or more and 90 nm or less, and the crystalline film has a thickness of 1 nm or more and 15 nm or less.

8. The semiconductor gas sensor according to claim 5, further comprising:
(g) a heater for heating the semiconductor gas sensor, wherein
the heater is composed of a laminate film in which a titanium film, a platinum film, and a molybdenum film are formed sequentially, a tungsten monolayer film, a laminate film in which a molybdenum film and a tungsten film are formed sequentially, or a laminate film in which a molybdenum film, a tungsten film, and a molybdenum film are formed sequentially.

9. A semiconductor gas sensor, comprising:
(a) a semiconductor layer;
(b) a capacitive insulating film formed on the semiconductor layer;
(c) a crystalline film formed on the capacitive insulating film;
(d) a gate electrode formed on the crystalline film;
(e) a source electrode adhered to the semiconductor layer; and
(f) a plurality of grain boundary regions, wherein
a capacitive element is formed from the source electrode and the gate electrode sandwiching the capacitive insulating film,
the crystalline film is composed of modified TiOx, the modified TiOx being formed from a TiOx microcrystalline region and an oxygen-doped amorphous Ti region, and the ratio of the TiOx microcrystalline region is 50% or more,
the gate electrode has a platinum film or an iridium film, the platinum film or the iridium film is composed of a plurality of crystal grains, and
at least one grain boundary region includes oxygen and titanium and is disposed between immediately adjacent crystal grains, the at least one grain boundary region preventing the formation of a gap between the immediately adjacent crystal grains.

10. The semiconductor gas sensor according to claim 9, wherein the semiconductor layer is composed of silicon or silicon carbide, and the capacitive insulating film is composed of silicon oxide.

11. The semiconductor gas sensor according to claim 9, wherein the platinum film or the iridium film has a thickness of 1 nm or more and 90 nm or less, and the crystalline film has a thickness of 1 nm or more and 15 nm or less.

12. A semiconductor gas sensor, comprising a first sensor section and a second sensor section formed on the same semiconductor substrate, wherein
the first sensor section includes:
(a) a semiconductor layer;
(b) a first gate insulating film formed on the semiconductor layer;
(c) a first crystalline film formed on the first gate insulating film;
(d) a first gate electrode formed on the first crystalline film;
(e) a first source region formed on the semiconductor layer;
(f) a first drain region formed on the semiconductor layer;
(g) an insulating film which covers the surface of the first gate electrode,
the second sensor section includes:
(h) the semiconductor layer;
(i) a second gate insulating film formed on the semiconductor layer;
(j) a second crystalline film formed on the second gate insulating film;
(k) a second gate electrode formed on the second crystalline film;
(l) a second source region formed on the semiconductor layer; and
(m) a second drain region formed on the semiconductor layer, and
a plurality of grain boundary regions, wherein
the surface of the second gate electrode is exposed,
the first crystalline film and the second crystalline are composed of modified TiOx, the modified TiOx being formed from a TiOx microcrystalline region and an oxygen-doped amorphous Ti region, and the ratio of the TiOx microcrystalline region is 50% or more,
the first gate electrode and the second gate electrode have a platinum film or an iridium film, the platinum film or the iridium film is composed of a plurality of crystal grains, and
at least one grain boundary region includes oxygen and titanium and is disposed between immediately adjacent crystal grains, the at least one grain boundary region preventing the formation of a gap between the immediately adjacent crystal grains.

* * * * *